(12) United States Patent
Weinberg et al.

(10) Patent No.: US 7,902,147 B2
(45) Date of Patent: Mar. 8, 2011

(54) CHRONIC LYMPHOCYTIC LEUKEMIA PROGNOSIS AND TREATMENT

(75) Inventors: J. Brice Weinberg, Durham, NC (US); Warren J. Strittmatter, Hillsborough, NC (US)

(73) Assignee: Duke University, Durham, NC (US)

( * ) Notice: Subject to any disclaimer, the term of this patent is extended or adjusted under 35 U.S.C. 154(b) by 14 days.

(21) Appl. No.: 12/265,079

(22) Filed: Nov. 5, 2008

(65) Prior Publication Data

US 2009/0136496 A1 May 28, 2009

Related U.S. Application Data

(60) Provisional application No. 60/985,365, filed on Nov. 5, 2007.

(51) Int. Cl.
*A01N 37/18* (2006.01)
(52) U.S. Cl. .................................... 514/2; 514/4
(58) Field of Classification Search ........................ None
See application file for complete search history.

(56) References Cited

U.S. PATENT DOCUMENTS

| | | | |
|---|---|---|---|
| 5,288,717 | A | 2/1994 | Raveendranath et al. |
| 5,422,119 | A | 6/1995 | Casper |
| 5,508,167 | A | 4/1996 | Roses et al. |
| 5,716,828 | A | 2/1998 | Roses et al. |
| 5,723,455 | A | 3/1998 | Tanabe et al. |
| 5,767,248 | A | 6/1998 | Roses et al. |
| 6,027,896 | A | 2/2000 | Roses et al. |
| 6,251,587 | B1 | 6/2001 | Sévigney et al. |
| 6,432,643 | B1 | 8/2002 | Einstein et al. |
| 6,828,103 | B2 | 12/2004 | Herrington et al. |
| 6,896,885 | B2 | 5/2005 | Hanna |
| 7,049,078 | B2 | 5/2006 | Poirier |
| 7,138,426 | B2 | 11/2006 | DiNinno et al. |
| RE39,419 | E | 12/2006 | Day et al. |
| 7,208,481 | B2 | 4/2007 | Phan et al. |
| 7,220,833 | B2 | 5/2007 | Nelson et al. |

OTHER PUBLICATIONS

DeKroon et al, J Lipid Res, 2003, 44:1566-1573.*
Freshney, Culture of Animal Cells, A Manual of Basic Technique, Alan R. Liss, Inc., 1983, New York, p4.*
Dermer, Bio/Technology, 1994, 12:320.*
Gura (Science, 1997, 278:1041-1042.*
Johnson and Tracey, 'Peptide and Protein Drug Delivery', In: Encyclopedia of Controlled Drug Delivery, vol. 2, 1999, pp. 816-833.*
Narasimhan P and Amaral L. Lymphopenic response of patients presenting with chronic lymphocytic leukemia associated with carcinoma of the prostate to diethylstilbestrol: correlation of response to the in vitro synthesis of rna by patient lymphocytes and its relationship to transcortin. American Journal of Hematology. 1980; 8(4): 369-375. Abstract only.
Rosen St et al. Estrogen receptor analysis in chronic lymphocytic leukemia. Blood. Nov. 1983; 62(5): 996-999.
Dallongeville J et al. Modulation of plasma triglyceride levels by apoE phenotype: a meta-analysis. Journal of Lipid Research. 1992; 33: 447-454.
Huang P et al. Superoxide dismutase as a target for the selective killing of cancer cells. Nature. Sep. 21, 2000; 407: 390-395.
Gruber CJ et al. Production and actions of estrogens. The New England Journal of Medicine. Jan. 31, 2002; 346(5): 340-352.
Raber J et al. Androgens protects against apolipoprotein E4-induced cognitive deficits. The Journal of Neuroscience. Jun. 15, 2002; 22(12): 5204-5209.
Dekroon RM et al. ApoE genotype-specific inhibition of apoptosis. Journal of Lipid Research. 2003; 44: 1566-1573.
Cuní S et al. A sustained activation of P13K/NF-\B pathway is critical for the survival of chronic lymphocytic leukemia B cells. Leukemia. 2004; 18: 1391-1400.
Robak T. Monoclonal antibodies in the treatment of chronic lymphoid leukemias. Leukemia & Lymphoma. Feb. 2004; 45(2): 205-219.
Chiorazzi N et al. Chronic lymphocytic leukemia. The New England Journal of Medicine. Feb. 24, 2005; 352(8): 804-815.
Gao N et al. 2-methoxyestradiol-induced apoptosis in human leukemia cells proceeds through a reactive oxygen species and Akt-dependent process. Oncogene. 2005; 24: 3797-3809.
Danilov AV et al. Molecular pathogenesis of chronic lymphocytic leukemia. Current Molecular Medicine. 2006; 6(6): 665-675.
Dekroon R et al. APOE-4-VLDL inhibits the HDL-activated phosphatidylinositol 3-kinase/akt pathway via the phosphoinositol phosphatase SHIP2. Circulation Research. Oct. 13, 2006; 829-836.
Wang JM et al. Activation of estrogen receptor $\alpha$ increases and estrogen receptor $\beta$ decreases apolipoprotein E expression in hippocampus in vitro and in vivo. PNAS. Nov. 7, 2006; 103(45): 169984-169988.
Weinberg JB et al. Apolipoprotein E (APOE) genotype as a determinant of survival in women with chronic lymphocytic leukemia. Blood (American Society of Hematology Annual Meeting Abstracts). 2007; 110: Abstract 3081.
Weinberg JB et al. Clinical and molecular predictors of disease severity and survival in chronic lymphocytic leukemia. American Journal of Hematology. 2007: 1063-1070.
Weinberg JB et al. Apolipoprotein E genotype as a determinant of survival in chronic lymphocytic leukemia. Leukemia. Leukemia. 2008; 1-9.

\* cited by examiner

*Primary Examiner* — Misook Yu
*Assistant Examiner* — Mark Halvorson
(74) *Attorney, Agent, or Firm* — Myers Bigel Sibley & Sajovec, P.A.

(57) ABSTRACT

Provided herein are methods for identifying a subject afflicted with chronic lymphocytic leukemia who is responsive to treatment with a chemotherapeutic agent by detecting the presence or absence of at least one APOE4 allele in the subject, the presence of an APOE4 allele identifying the subject as responsive to the treatment. Also provided are methods of treating a subject afflicted with chronic lymphocytic leukemia, including administering an estrogenic agent, an androgen withdrawal agent, an apoE4 peptide or mimetic thereof, and/or a chemotherapeutic agent in an amount effective to treat said chronic lymphocytic leukemia. Methods of determining a prognosis for a patient diagnosed with chronic lymphocytic leukemia are also provided. In addition, methods for stratifying a subject into a subgroup of a clinical trial and methods for identifying a patient in a clinical trial of a treatment for chronic lymphocytic leukemia are herein provided.

15 Claims, 8 Drawing Sheets

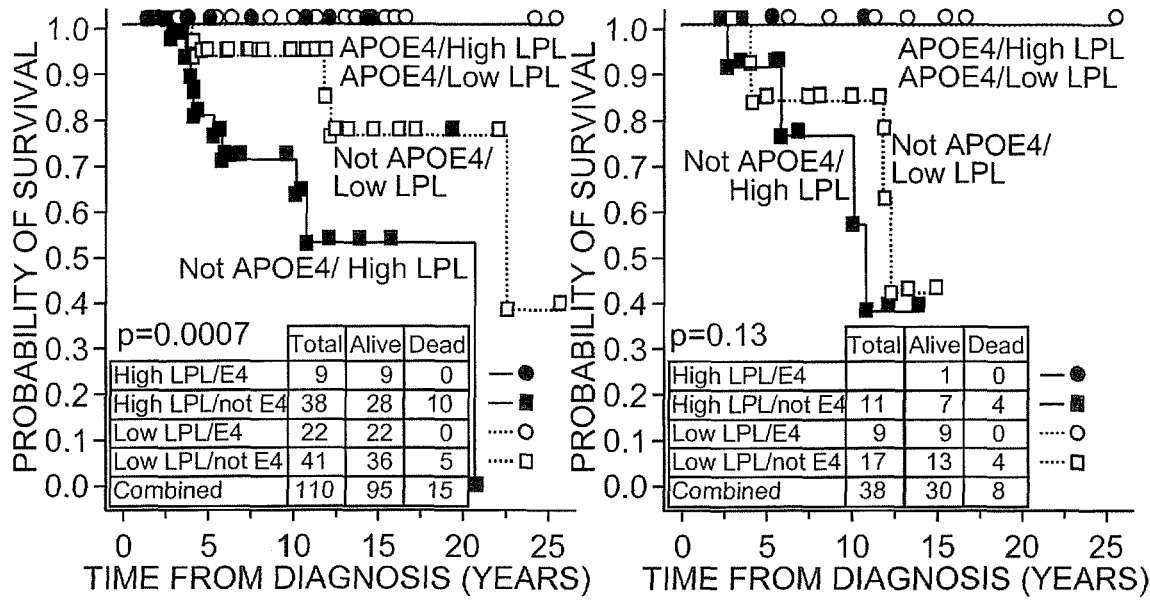
FIG. 4A
FIG. 4B
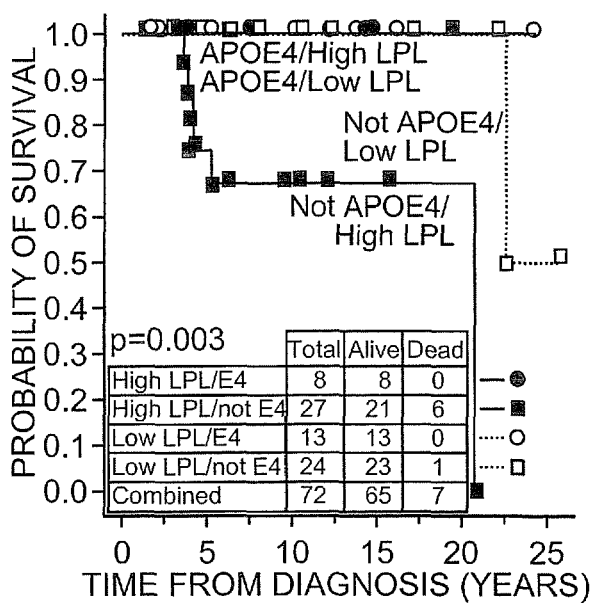
FIG. 4C

CHRONIC LYMPHOCYTIC LEUKEMIA PROGNOSIS AND TREATMENT

RELATED APPLICATIONS

This application claims the benefit under 35 U.S.C. §119 (e) of U.S. Provisional Patent Application Ser. No. 60/985,365, filed Nov. 5, 2007, the disclosure of which is incorporated herein by reference in its entirety.

STATEMENT OF GOVERNMENT SUPPORT

This invention was made with Government support under NIH grant number CA90548. The Government has certain rights to this invention.

FIELD OF THE INVENTION

The present invention concerns the prognosis and treatment of subjects afflicted with chronic lymphocytic leukemia.

BACKGROUND OF THE INVENTION

B-cell chronic lymphocytic leukemia (CLL), the most common leukemia in North America, is a disease of CD5+ B lymphocytes characterized by slow proliferation and decreased apoptosis. The decreased apoptotic death of CD5+ B lymphocytes contributes to their increased abundance in blood, producing the clinical entity of CLL.

The progression of this disorder is often indolent, with a median survival over 20 years from the time of diagnosis (Chiorazzi et al. (2005) N Engl J Med 352, 804-15; Keating, M. J. (2002) in Leukemia, eds. Henderson et al. (Saunders, Philadelphia), pp. 131-151). CLL is characterized by overexpression of anti-apoptotic proteins such as bcl-2, and commonly employed therapies in CLL increase apoptotic cell death. Activation of the PI-3-K/Akt pathway in CLL cells can inhibit apoptotic death (Cuni et al. (2004) Leukemia 18, 1391-400).

Many therapies for CLL cause leukemia cell death by triggering apoptosis. However, there is need for more effective prognosis and treatment options for diseases such as CLL.

SUMMARY OF THE INVENTION

Provided herein are methods for identifying a subject (e.g., a human subject) responsive to treatment with a chemotherapeutic agent, wherein the subject is afflicted with chronic lymphocytic leukemia, including detecting the presence or absence of at least one APOE4 allele in a biological sample of the subject, wherein the presence of at least one APOE4 allele identifies the subject as a subject whose chronic lymphocytic leukemia is responsive to treatment with the chemotherapeutic agent. In some embodiments, the subject is female. In some embodiments, the subject is male. In some embodiments, the subject is an adult or geriatric subject. In some embodiments, the subject is a postmenopausal female subject.

In some embodiments the methods include administering to a subject with at least one APOE4 allele a chemotherapeutic agent (e.g., bendamustine, flavopiridol, fludarabine, chlorambucil, cyclophosphamide, doxorubicin, prednisone, vincristine, monoclonal antibodies such as rituximab, alemtuzumab, lumiliximab, epratuzumab, ofatumumab, etc.) in an amount effective to treat said chronic lymphocytic leukemia.

Also provided are methods of treating a subject afflicted with chronic lymphocytic leukemia including: (i) detecting the presence or absence of an APOE4 allele in a biological sample of said subject (e.g., by genotyping); and (ii) administering (e.g., by oral or parenteral administration) to said subject an estrogenic agent or androgen withdrawal agent in an amount effective to treat said chronic lymphocytic leukemia.

Further provided are methods of treating a subject afflicted with chronic lymphocytic leukemia including administering to the subject apoE4 or mimetic thereof (e.g., by oral or parenteral administration) in an amount effective to treat the chronic lymphocytic leukemia. In some embodiments, the methods include detecting the presence or absence of at least one APOE4 allele in a biological sample of the subject (e.g., by genotyping).

Methods of treating a subject afflicted with chronic lymphocytic leukemia are provided, including administering to said subject apoE4 or a mimetic thereof in combination with administering to the subject an estrogenic agent or androgen withdrawal agent, the two combined in an amount effective to treat the chronic lymphocytic leukemia.

Methods of determining a prognosis for a patient diagnosed with chronic lymphocytic leukemia are also provided, including obtaining a patient profile (e.g., including detecting the presence or absence of at least one APOE4 allele in a biological sample of the patient, determining the gender of the patient, etc.), and then converting the patient profile into the prognosis, wherein the presence of said APOE4 allele identifies the subject as a subject whose chronic lymphocytic leukemia is responsive to treatment with one or more chemotherapeutic agents. In some embodiments, obtaining the patient profile also includes detecting one or more factors selected from the group consisting of: LPL mRNA level, clinical stage, lymphocyte doubling time, immunoglobulin $IgV_H$ mutation status, cytogenetic abnormalities, leukemia cell CD38 expression and Zap-70 expression.

Further provided are methods for stratifying a subject into a subgroup of a clinical trial of a therapy for the treatment of chronic lymphocytic leukemia, including detecting the presence or absence of at least one APOE4 allele in a biological sample of the subject, wherein the subject is stratified into said subgroup for said clinical trial of said therapy based upon the presence or absence of said at least one APOE4 allele. In some embodiments, the therapy includes administering a chemotherapeutic agent.

In some embodiments, the methods include determining the gender of the subject, wherein the subject is stratified into said subgroup for said clinical trial of said therapy based upon both: (a) the presence or absence of said at least one APOE4 allele; and (b) the gender of said patient.

Methods are also provided for identifying a patient in a clinical trial of a treatment for chronic lymphocytic leukemia, including: (a) identifying a patient diagnosed with chronic lymphocytic leukemia; and (b) determining a prognosis for the patient diagnosed with chronic lymphocytic leukemia, including obtaining a patient profile (e.g., including detecting the presence or absence of at least one APOE4 allele in a biological sample of the patient, determining the gender of the patient, etc.), wherein the prognosis includes a prediction of whether the patient is a candidate for the clinical trial. In some embodiments, obtaining the patient profile also includes detecting one or more factors selected from the group consisting of: LPL mRNA level, clinical stage, lymphocyte doubling time, immunoglobulin $IgV_H$ mutation status, cytogenetic abnormalities, leukemia cell CD38 expression and Zap-70 expression.

A further aspect of the present invention is the use of active agents as described herein for the preparation of a medicament for carrying out a method of treatment for chronic lymphocytic leukemia as described herein.

The present invention is explained in greater detail in the drawings herein and in the specification set forth below.

BRIEF DESCRIPTION OF THE DRAWINGS

FIG. 4. APOE4 genotype/LPL and survival. 4A. APOE4/LPL and survival in the entire cohort. 4B. APOE4/LPL and survival in females only. 4C. APOE4/LPL and survival in men only. The data are from subjects on whom we performed both APOE genotyping and LPL mRNA quantitation.

DETAILED DESCRIPTION OF THE PREFERRED EMBODIMENTS

Figure 1A:
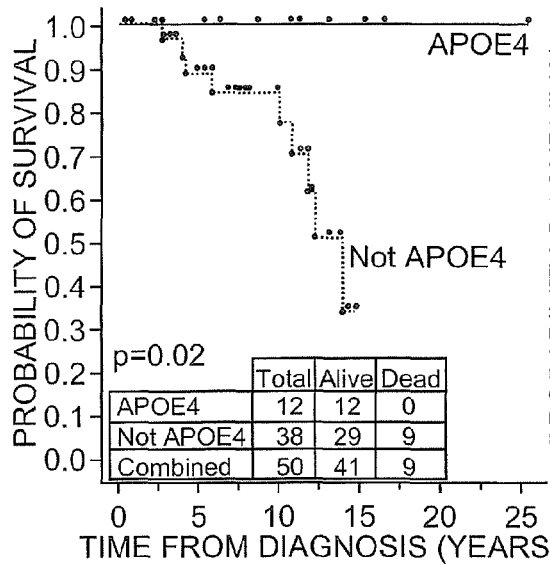
FIG. 1. APOE4, survival, and time-to-treatment (TTT). 1A. APOE4 and survival in females only. 1B. APOE4 and survival in males only. 1C. APOE4 and TTT in the women only. 1D. APOE4 and TTT in men only.

The present inventors have discovered a significant association between the APOE4 genotype and responsiveness to treatment and survival among patients afflicted with chronic lymphocytic leukemia (CLL). Without wishing to be bound by theory, it is hypothesized that the beneficial effect of an APOE4 genotype is mediated through regulation of leukemia cell apoptosis. Our studies suggest that the APOE4 genotype does not alter susceptibility to developing CLL, but does influence CLL outcome and response to therapies. The present inventors have also discovered that apoE4 (protein) is cytotoxic for CLL cells in vitro, but apoE3 is not cytotoxic for CLL cells in vitro.

The present inventors have also discovered an unexpected and striking gender difference in the influence of the APOE4 genotype. Women, but not men, with an APOE4 genotype had markedly longer survival than non-APOE4 patients. This female-specific protective effect may relate to the modulation of CLL cell apoptosis by estrogens.

All United States Patent references cited herein are to be incorporated by reference herein in their entirety to the extent they are consistent with the disclosure herein.

"Chronic lymphocytic leukemia" or "CLL" is a slow-growing type of leukemia (blood cancer) in which too many lymphoblasts (immature white blood cells) are found in the blood and/or bone marrow. It is a disease of CD5+ B lymphocytes characterized by slow proliferation and decreased apoptosis. CLL is currently an incurable disease, and the decision to treat this leukemia is based on a variety of factors including decline in other blood elements (e.g., development of anemia or thrombocytopenia), increasing lymphocyte count rates (e.g., a lymphocyte doubling time of less than 1 year), and systemic side effects such as fever and weight loss (Cheson et al. (1996) Blood 87, 4990-7). Clinical stage, lymphocyte doubling time, immunoglobulin $IgV_H$ mutation status, cytogenetic abnormalities, and leukemia cell CD38 and Zap-70 expression are significantly associated with survival in CLL (Chiorazzi et al. (2005) N Engl J Med 352, 804-15; Keating, M. J. (2002) in Leukemia, eds. Henderson et al. (Saunders, Philadelphia), pp. 131-151).

"Treating" refers to any type of treatment that imparts a benefit to a patient, e.g., a patient afflicted with a disease (e.g., a leukemia). A subject is "responsive" to treatment if the treatment results in a benefit to the subject, e.g., increases the rate or probability of survival across a period of time (e.g., 10, 20 or 30 years from diagnosis). Treating includes actions taken and actions refrained from being taken for the purpose of improving the condition of the patient (e.g., the relief of one or more symptoms), delay in the onset or progression of the disease, lessening of one or more symptoms associated with the disease, etc. In some embodiments, treating CLL includes the administration of an active agent (e.g., apoE4, estrogen, etc.) to a subject in need thereof. In some embodiments treating CLL further includes the administration of a chemotherapeutic agent. This may be accomplished by, e.g., the combination therapies described below.

The administration of two or more compounds "in combination" or "in conjunction" means that the two compounds are administered closely enough in time to have an additive and/or synergistic effect. The two compounds may be administered simultaneously (concurrently) or sequentially. Simultaneous administration may be carried out by mixing the compounds prior to administration, or by administering the compounds at the same point in time but at different anatomic sites or using different routes of administration.

"Pharmaceutically acceptable" as used herein means that the compound or composition is suitable for administration to a subject to achieve the treatments described herein, without unduly deleterious side effects in light of the severity of the disease and necessity of the treatment. "Prodrug" refers to compounds that are rapidly transformed in vivo to yield an active agent, for example, by hydrolysis in blood.

The "time-to-treatment" or "TTT" refers to the length of time between the date of diagnosis and initiation of medical treatment (e.g., by administering one or more chemotherapeutic agents). Treatment of CLL typically ranges from periodic observation with treatment of infectious, hemorrhagic, or immunologic complications, to a variety of therapeutic options, including chemotherapies such as alkylating agents, purine analogs, combination chemotherapy and monoclonal antibodies, as well as transplant options. Because this disease is generally not curable, typically occurs in middle-aged and elderly adults, and often progresses slowly, it is most often treated in a conservative fashion.

"Subjects" are, in general, human subjects (including "patients"), or other animal subjects (e.g., laboratory animals), and particularly mammalian subjects such as dogs, cats, rabbits, horses, cattle, sheep, etc. for veterinary purposes. In some embodiments, subjects are female. In other embodiments, subjects are male. Subjects may be of any age, including juvenile, adolescent, teenage, young adult, adult, middle-age, elderly and geriatric subjects. Human subjects may also be of any ethnicity, e.g., Caucasian, African-American, Hispanic, Asian, Indian, etc. In some embodiments, human subjects are at least 16, 18, 25 or 30 years of age. In other embodiments, human subjects are at least 35, 40, 45 or 50 years of age. In further embodiments, human subjects are at least 60 or 65 years of age. In some embodiments, human subjects are postmenopausal female subjects.

"Apolipoprotein E" or "apoE" is a protein that combines with and transports fats (lipids) in the body. There are at least three isoforms of the APOE gene which encodes the apoE protein: APOE2, APOE3 and APOE4. APOE3 is the most common allele in humans.

The "apoE4" isoform of the lipoprotein apoE has been previously implicated as a predisposing factor in Alzheimer's disease and in the development of atherosclerosis. ApoE4 has been shown to evoke apoptosis in neuronal cells through the LDL receptor-related protein (LRP) and heterotrimeric GTPases (Hashimoto et al. (2000) J. Neurosci. 20, 8401-8409). Antisense oligonucleotides to LRP mRNA and the presence of LRP-associated protein RAP (receptor associated protein) inhibit apoE4-induced apoptosis (Hashimoto et al. (2000) J. Neurosci. 20, 8401-8409).

Blood lipoprotein particles can be either pro- or anti-apoptotic. High density lipoprotein (HDL) particles, interacting through a sphingosine-1-phosphate receptor 3 ($SIP_3$), can inhibit apoptosis by activating the PI-3-K/Akt pathway (4). Very low density lipoprotein (VLDL) particles containing apolipoprotein E4 (apoE4) (but not the apoE3 or apoE2 isoforms) inhibit this PI-3-K/Akt pathway. ApoE4 VLDL cell surface binding can recruit the phosphoinositol phosphatase SHIP-2 to the plasma membrane, causing a decrease in PIP3 and subsequent reduction in phosphorylation of Akt. These events can result in increased apoptosis (DeKroon et al. (2006) Circ Res 99, 829-36). VLDL is metabolized to low density lipoproteins (LDL) through lipoprotein lipase (LPL).

"Lipoprotein lipase" or "LPL" is a secreted enzyme that hydrolyzes phospholipids in VLDL particles, thereby increasing serum triglycerides and converting VLDL particles to LDL particles. Higher levels of leukemia cell LPL mRNA are generally associated with a shorter survival and shorter TTT in CLL.

"Genotyping" or genotype determination of subjects (i.e., determining or detecting whether or not a subject carries one, two, or no APOE4 alleles) can be carried out in accordance with known techniques, e.g., as described in U.S. Pat. Nos. 6,027,896 and 5,508,167. Genotyping herein includes "phenotyping" by determining or detecting which apoE protein is expressed (e.g., by using apoE isoform-specific antibodies, such as those described in U.S. Pat. Nos. 5,767,248 and 5,716,828 to Roses et al.), thereby indicating the presence of one or more APOE4 alleles.

"Active agents" of the present invention include any compound that promotes the binding of apoE4 to cell surface LDL receptors, or promotes upstream or downstream signaling associated with the presence of the apoE4 protein. See, e.g., U.S. Pat. Nos. 7,220,833 and 7,208,481. Examples of active agents include, but are not limited to, apoE4 (e.g., VLDL-apoE4) and mimetics thereof.

"Mimetics" of apoE4 are those compounds which are capable of binding LDL receptors and/or promote upstream or downstream signaling associated with the presence of the apoE4 protein. Mimetics may be developed, e.g., by generating a library of molecules, selecting for those molecules which act as agonists, and identifying and amplifying the selected agonists. See, e.g., Kohl et al., Science 260, 1934 (1993) (synthesis and screening of tetrapeptides for inhibitors of farnesyl protein transferase, to inhibit ras oncoprotein dependent cell transformation). Techniques for constructing and screening combinatorial libraries of oligomeric biomolecules to identify those that specifically bind to a given receptor protein are known. Suitable oligomers include peptides, oligonucleotides, carbohydrates, nonoligonucleotides (e.g., phosphorothioate oligonucleotides; see Chem. and Engineering News, page 20, Feb. 7, 1994) and nonpeptide polymers (see, e.g., "peptoids" of Simon et al., Proc. Natl. Acad. Sci. USA 89, 9367 (1992)). See also U.S. Pat. No. 5,270,170 to Schatz; Scott and Smith, Science 249, 386-390 (1990); Devlin et al., Science 249, 404-406 (1990); Edgington, BIO/Technology 11, 285 (1993). Peptide libraries may be synthesized on solid supports, or expressed on the surface of bacteriophage viruses (phage display libraries). Known screening methods may be used by those skilled in the art to screen combinatorial libraries to identify antagonists. Techniques are known in the art for screening synthesized molecules to select those with the desired activity, and for labeling the members of the library so that selected active molecules may be identified. See, e.g., Brenner and Lerner, Proc. Natl. Acad. Sci. USA 89, 5381 (1992) (use of genetic tag to label molecules in a combinatorial library); PCT US93/06948 to Berger et al., (use of recombinant cell transformed with viral transactivating element to screen for potential antiviral molecules able to inhibit initiation of viral transcription); Simon et al., Proc. Natl. Acad. Sci. USA 89, 9367 (1992) (generation and screening of "peptoids", oligomeric N-substituted glycines, to identify ligands for biological receptors); U.S. Pat. No. 5,283,173 to Fields et al. (use of genetically altered *Saccharomyces cerevisiae* to screen peptides for interactions).

In protein or peptide molecules which interact with a receptor, the interaction between the protein or peptide and the receptor generally takes place at surface-accessible sites in a stable three-dimensional molecule. By arranging the critical binding site residues in an appropriate conformation, mimetics that have the essential surface features of the peptides described herein may be generated and synthesized in accordance with known techniques. Methods for determining peptide three-dimensional structure and analogs thereto are known, and are sometimes referred to as "rational drug design techniques." See, e.g., U.S. Pat. No. 4,833,092 to Geysen; U.S. Pat. No. 4,859,765 to Nestor; U.S. Pat. No. 4,853,871 to Pantoliano; U.S. Pat. No. 4,863,857 to Blalock; (applicants specifically intend that the disclosures of all U.S. Patent references cited herein be incorporated by reference herein in their entirety). See also Waldrop, Science 247, 28029 (1990); Rossmann, Nature 333, 392 (1988); Weis et al., Nature 333, 426 (1988); James et al., Science 260, 1937 (1993) (development of benzodiazepine peptidomimetic compounds based on the structure and function of tetrapeptide ligands).

In general, those skilled in the art will appreciate that minor deletions or substitutions may be made to the amino acid sequences of proteins or peptides of the present invention without unduly adversely affecting the activity thereof. Thus, peptides containing such deletions or substitutions are a further aspect of the present invention. In peptides containing substitutions or replacements of amino acids, one or more amino acids of a peptide sequence may be replaced by one or more other amino acids wherein such replacement does not affect the function of that sequence. Such changes can be guided by known similarities between amino acids in physical features such as charge density, hydrophobicity/hydrophilicity, size and configuration, so that amino acids are substituted with other amino acids having essentially the same functional properties. For example: Ala may be replaced with Val or Ser; Val may be replaced with Ala, Leu, Met, or Ile, preferably Ala or Leu; Leu may be replaced with Ala, Val or Ile, preferably Val or Ile; Gly may be replaced with Pro or Cys, preferably Pro; Pro may be replaced with Gly, Cys, Ser, or Met, preferably Gly, Cys, or Ser; Cys may be replaced with Gly, Pro, Ser, or Met, preferably Pro or Met; Met may be replaced with Pro or Cys, preferably Cys; His may be replaced with Phe or Gln, preferably Phe; Phe may be replaced with His, Tyr, or Trp, preferably His or Tyr; Tyr may be replaced with His, Phe or Trp, preferably Phe or Trp; Trp may be replaced with Phe or Tyr, preferably Tyr; Asn may be replaced with Gln or Ser, preferably Gln; Gln may be replaced with His, Lys, Glu, Asn, or Ser, preferably Asn or Ser; Ser may be replaced with Gln, Thr, Pro, Cys or Ala; Thr may be replaced with Gln or Ser, preferably Ser; Lys may be replaced with Gln or Arg; Arg may be replaced with Lys, Asp or Glu, preferably Lys or Asp; Asp may be replaced with Lys, Arg, or Glu, preferably Arg or Glu; and Glu may be replaced with Arg or Asp, preferably Asp. Once made, changes can be routinely screened to determine their effects on function.

"Estrogenic agents" refers to compounds which activate estrogen receptors and/or are structurally similar to (e.g., are derived from) estrogen (e.g., estrogen receptor agonists). Examples include, but are not limited to, estrogen and estrogen analogs. See U.S. Pat. No. 6,432,643 to Einstein et al.

Without wishing to be bound to a particular theory, the female-specific protective effective of the APOE4 genotype on survival in CLL could relate to several mechanisms, including modulation of CLL cell apoptosis by estrogen through the apoE/Akt pathway. Some studies have indicated that estrogens can be cytotoxic for CLL cells in vitro (Huang et al. (2000) Nature 407, 390-5), and diethylstilbestrol treatment of prostate cancer in patients with CLL has been reported to reduce blood CLL cell counts (Narasimhan et al. (1980) Am J Hematol 8, 369-75). Several physiological metabolites of endogenous estrogen (including 2-methoxyestradiol) induce apoptosis of leukemia cells by inactivating Akt (Gao et al. (2005) Oncogene 24, 3797-809). Estrogen receptor agonists stimulate PIP3 synthesis and enhances Akt phosphorylation in endothelial cells (Haynes et al. (2000) Circ Res 87, 677-82). We have shown that Akt phosphorylation is inhibited by APOE4-VLDL (DeKroon et al. (2006) Circ Res 99, 829-36). Estrogen regulates APOE expression (Wang et al. (2006) Proc Natl Acad Sci USA 103, 16983-8). Androgen interacts with apolipoprotein genotype, protecting against APOE4-induced cognitive deficits (Raber et al. (2002) J Neurosci 22, 5204-9). The APOE genotype alters lipoprotein particle distribution and number, and triglyceride metabolism, and gender differences in these effects have been reported (Dallongeville et al. (1992) J Lipid Res 33, 447-54; Ferrieres et al. (1994) Arterioscler Thromb 14, 1553-60). These observations suggest that the female-specific protective effective of the APOE4 genotype on survival in CLL could relate to the modulation of CLL cell apoptosis by estrogen through the apoE/Akt pathway.

"Estrogen" includes, but is not limited to, naturally occurring estrogens such as estradiol ($E_2$), estrone ($E_1$), and estriol ($E_3$), synthetic conjugated estrogens, oral contraceptives and sulfated estrogens. See, e.g., Gruber et al. (2002) N Engl J Med 346, 340-352.

"Analogs" of estrogen are compounds that are estrogen-like in that they have at least one of the effects of estrogen, e.g., bind to one or more types of estrogen receptors in the body (e.g., diethylstilbestrol), and/or are structurally similar to estrogen (e.g., 2-methoxyestradiol). Natural and synthetic estrogens include, but are not limited to, conjugated equine estrogen, ethinyl estradiol, micronized estradiol, 17 β estradiol, mestranol, estradiol valerate, 11-nitrato estradiol, 7-α-methyl-11-nitrato-estradiol, piperazine estrone sulfate, quinestranol, and 8,9-dehydroestereone (particularly alkali metal salts and sulfate esters thereof). See, e.g., U.S. Pat. No. 5,422,119 at column 6; U.S. Pat. Nos. 5,288,717; 7,138,426 to DiNinno et al.; U.S. Pat. No. RE39,419 to Day et al.

"Estrogen replacement therapy" (sometimes also referred to as "hormone replacement therapy" or HRT) refers to a long-term therapy in which estrogen or estrogenic agents are administered to a subject continuously over an extended period of time (e.g., one month, one year, or more) to maintain sustained blood levels of the agent, e.g., to combat the effects of menopause or hysterectomy which may include the loss of calcium from bone and increased incidence of classical osteoporotic fractures of the forearm and hip, ischemic heart disease, etc. Administration may be daily or periodically in some embodiments. See, e.g., U.S. Pat. No. 6,828,103 to Herrington et al.

Administration of estrogen to men and/or the withdrawal of androgen in men is also contemplated. The withdrawal of androgen in men is known in the art, for example, in the context of treatment for prostate cancer, by e.g., castration, alterations in gene expression and/or through the use of an anti-androgenic drug. Accordingly, "androgen withdrawal agents" are administered in one aspect of the present invention. Androgen withdrawal agents, include, but are not limited to, an anti-androgenic drug, including, but not limited to, casodex, nafarelin, leuprolide, goserelin, buserelin, cyproterone acetate, zanoterone, megestrol acetate, hydroxy-progesterone caproate, medrogestone, hydroxyflutamide, Casodex.RTM, nilutamide, finasteride, etc. See, e.g., U.S. Pat. No. 7,250,180 to Arellano; U.S. Pat. No. 5,723,455 to Tanabe et al.

Active agents may be prepared as a pharmaceutically acceptable salt or ester, in accordance with known techniques. Dosage of the active agent will depend, among other things, the condition of the subject as well as other factors that may be considered to make a prognosis. Optimization of dosages are within the skill of those in the relevant art.

Combination Therapies.

In some embodiments active agents are administered in conjunction with one or more chemotherapeutic agents and/or radiation therapy and/or transplantation (e.g., stem cell transplantation), as is known in the art pertaining to the treatment of leukemias.

"Chemotherapeutic" or "antineoplastic" agents as used herein refer to agents in addition to or other than the active agents described above (apoE4 or mimetics thereof, estrogenic agents, androgen withdrawal agents, etc). Chemotherapeutic agents are well known in the art, and include, but are not limited to, alkylating agents (e.g., platinum alkylating agents, nitrosaurea alkylating agents, nitrogen mustard alkylating agents, etc.), antimetabolites (e.g., purine, pyrimidine, folic acid, etc.), antibiotic agents (e.g., anthracycline antibiotics, etc.), plant alkaloids (e.g., vinca alkaloids, taxane alkaloids, etc.), topoisomerase inhibitors (e.g., camptotheca, podophyllum, etc.), immunotherapy agents, kinase inhibitors (e.g., cyclin-dependent kinase (cdk) inhibitors such as rocovitine, flavopiridol, etc.), and others (e.g., UCS-01, altretamine, amsacrine, maytansine, etc.). See also U.S. Patent Application Publication No. 2006/0121539 to Debinski et al. at paragraph [0076]; U.S. Patent Application Publication No. 2007/0219268 to Hausheer at paragraph [0119].

Examples of alkylating agents include, but are not limited to, BBR3464, bendamustine, busulfan, carboplatin, carmustine, chlorambucil, cisplatin, cyclophosphamide, dacabazine, fotemustine, ifosfamide, lomustine, mechlorethamine hydrochloride, melphalan, oxaliplatin, procarbazine, streptozotocin, temozolomide, thiotepa, uracil mustard, etc. Examples of antimetabolites include, but are not limited to, aminopterin, capecitabine, cladribine, clofarabine, cytarabine, floxuridine, fludarabine phosphate, fluorouracil, gemcitabine, hydroxyurea, mercaptopurine, methotrexate, pemetrexed, raltitrexed, thioguanine, etc. Examples of antibiotic agents include, but are not limited to, actinomycin-D, bleomycin, daunorubicin, doxorubicin, epirubicin, idarubicin, mitomycin, mitoxantrone, pentostatin, plicamycin, valrubicin, etc. Examples of plant alkaloids include, but are not limited to, docetaxil, paclitaxil, vinblastine, vincristine, vindesine, vinorelbine, etc. Examples of topoisomerase inhibitors include, but are not limited to, camptothecin, etoposide, irinotecan, teniposide, topotecan, etc.

Examples of immunotherapy chemotherapeutic agents include, but are not limited to, alemtuzumab, bevcizumab, cetuximab, gemtuzumab, ofatumumab, ozogamisin, penitumumab, rituximab, tositumomab, trastuzumab, etc. Monoclonal antibodies directed against the CD20 (rituximab, RIT) and CD52 antigens (campath-1H, alemtuzumab, ALT) have shown beneficial activity in chronic lymphocytic leukemia (Robak (2004) Leukemia & Lymphoma 45, 205-219). Monoclonal antibodies directed against the CD23 antigen (Lumiliximab) and CD22 antigen (Epratuzumab) have also been developed. Other antigens to which antibodies have been prepared (e.g., for treating B cell leukemias) include, but are not limited to, CD21, CD23, CD22, CD19, CD40, CD37, etc. See, e.g., U.S. Pat. No. 6,896,885 to Hanna.

Formulations and Administrations.

The present invention may be carried out in like manner as described in U.S. Pat. No. 6,514,992 to Lee et al. For therapeutic use the active agents of the present invention will generally be administered in a standard pharmaceutical composition obtained by admixture with a pharmaceutical carrier or diluent selected with regard to the intended route of administration and standard pharmaceutical practice. For example, they may be administered orally in the form of tablets containing such excipients as starch or lactose, or in capsule, ovules or lozenges either alone or in admixture with excipients, or in the form of elixirs or suspensions containing flavoring or coloring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood. The choice of form for administration as well as effective dosages will vary depending, inter alia, on the condition being treated. The choice of mode of administration and dosage is within the skill of the art.

The compounds contemplated for use according to the present invention or their pharmaceutically acceptable salts which are active when given orally, can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerin, non-aqueous solvent, for example polyethylene glycol, oils, or water with a suspending agent, preservative, flavoring or coloring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule. Preferably the composition is in unit dose form such as a tablet or capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

A typical suppository formulation comprises a compound or a pharmaceutically acceptable salt thereof which is active when administered in this way, with a binding and/or lubricating agent such as polymeric glycols, gelatins or cocoa butter or other low melting vegetable or synthetic waxes or fats.

The pharmaceutically acceptable compounds of the invention will normally be administered to a subject in a daily dosage regimen. For a patient this may be, for example, from about 0.001 to about 100 mg/kg, preferably from about 0.001 to about 10 mg/kg animal body weight. A daily dose, for a larger mammal is preferably from about 1 mg to about 1000 mg, preferably between 1 mg and 500 mg or a pharmaceutically acceptable salt thereof, calculated as the free base, the compound being administered 1 to 4 times per day. Unit dosage forms may contain from about 25 µg to about 500 mg of the compound.

The active agents may be administered by any medically appropriate procedure, e.g., normal intravenous or intra-arterial administration.

Active agents may be provided in lyophilized form in a sterile aseptic container or may be provided in a pharmaceutical formulation in combination with a pharmaceutically acceptable carrier, such as sterile pyrogen-free water or sterile pyrogen-free physiological saline solution.

Methods of Determining a Prognosis.

To determine a prognosis (the prospect of recovery as anticipated from the usual course of disease or peculiarities of the case) according to some embodiments of the present invention, diagnostic data, including the patient's diagnosis and genetic data, such as the patient's APOE genotype, may be processed to provide therapeutic options and outcome predictions. Processing may include obtaining a "patient profile" such as the collection of a patient's medical history including age and gender, APOE genotyping (e.g., using appropriately designed primers and using an RT-PCR or PCR amplification step and/or apoE phenotyping, e.g., using an antibody-mediated method or enzymatic test), and statistical or other analyses that converts this raw data into a prognosis. The prognosis may include a prediction of a patient's response to drug therapy, recovery time, time to treatment, treatment efficacy, rehabilitation time, etc. For example, the presence of an APOE4 allele could be used by those of skill in the art (e.g., treating physicians) as a positive predictor for CLL patients that respond well to chemotherapeutic therapy. In some embodiments, the prognosis may include the use of a computer software program to analyze patient data and run statistical cross-checks against relational databases in order to convert the patient data or profile to a prognosis.

A "patient profile" includes data and/or materials pertaining to the patient for whom the prognostic analysis is being performed. Data may include information on the patient's diagnosis, age, gender, and/or APOE genotype. The patient profile may also include materials from the patient such as blood, serum protein samples, cerebrospinal fluid, or purified RNA or DNA.

"Factors" that are significantly associated with survival in CLL patients include, but are not limited to, clinical stage, lymphocyte doubling time, immunoglobulin $IgV_H$ mutation status, cytogenetic abnormalities, and leukemia cell CD38 and Zap-70 expression (see, e.g., Chiorazzi et al. (2005) N Engl J Med 352, 804-15; Keating, M. J. (2002) in Leukemia, eds. Henderson et al. (Saunders, Philadelphia), pp. 131-151; Damle et al. (1999) Blood. 94, 1840-1847; Hamblin et al. (1999) Blood. 94, 1848-1854; Dohner et al. (2000) New England Journal of Medicine 343, 1910-1916; Weinberg et al. (2007) Am J Hematol 82, 1063-1070). LPL mRNA levels may also be included as a factor to determine the prognosis of a patient diagnosed with CLL.

Detecting APOE4 Genotype in Clinical Trials.

In addition to use in the prognosis and/or treatment for CLL, detection of an APOE4 genotype can be used in conducting a clinical trial in like manner as other genotype information is used to conduct a clinical trial, such as described in, e.g., U.S. Pat. Nos. 6,573,049 6,368,797 and 6,291,175.

In some embodiments, such methods advantageously stratify or permit the refinement of the patient population (e.g., by division of the population into one or more subgroups) so that advantages of particular treatment regimens can be more accurately detected, particularly with respect to particular sub-populations of patients. In some embodiments, such methods comprise administering a test active agent or therapy to a plurality of subjects (a control or placebo therapy typically being administered to a separate but similarly characterized plurality of subjects) and detecting the presence or absence of an APOE4 genotype as described above in the plurality of subjects. The APOE4 genotype may be detected before, after, or concurrently with the step of administering the test therapy. The influence of one or more detected APOE4 alleles on the test therapy can then be determined on any suitable parameter or potential treatment outcome or consequence, including, but not limited to, the efficacy of said therapy, lack of side effects of the therapy, etc.

Accordingly, in some embodiments, knowing or detecting APOE genotypes in a randomized research trial will helps investigators balance groups to avoid any bias introduced by certain prognostic factors. For example, in an embodiment comparing treatments X and Y, there should be an equal number of APOE4 women in both limbs of the trial. Otherwise, if treatment X group had more APOE4 women, it would appear that treatment X was better than treatment Y, when the results were, in fact, biased by the number of APOE4 women in the respective groups.

A clinical trial can be set up to test the efficacy of test compounds to treat any number of diseases for which an APOE genotype has been determined to be associated with a subject diagnosed with a disease or at risk for developing the disease. If subjects are genotyped after the completion of a clinical trial, the analyses may still be aimed at determining a relationship between a treatment for a disease and the allele to be assessed for efficacy. Alternatively, if a symptomatic subject has not yet been diagnosed with the disease but has been determined to be at risk, a similar clinical trial to the clinical trial described above may be carried out.

Assessment of the efficacy of a drug chosen for the trial may include monitoring the subject over a period of time and analyzing the delay of onset of the disease and the intensity of the disease at the time of onset, as well as measuring the onset of symptoms which are associated with the disease. A drug that, in a clinical trial, eliminates or delays the onset of the disease, or reduces the symptoms of the disease may be a beneficial drug to use in patients diagnosed with the disease. Test compounds which may be used in such trials include chemotherapeutic agents as described above, including those previously approved for clinical use and new compounds not yet approved for use, or approved for treating CLL in particular. Thus, in some embodiments the clinical trial may include the optimization of drug administration, including dosage, timing of administration, toxicities or side effects, route of administration, and efficacy of the treatment.

The present invention is explained in greater detail in the following non-limiting Examples.

EXAMPLE 1

Figure 1B:
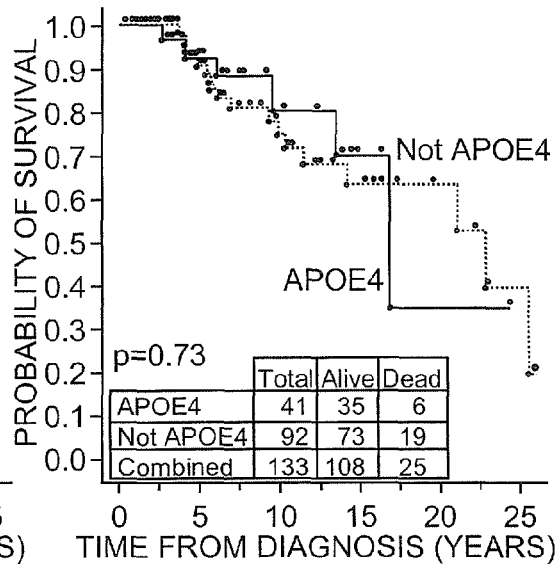
Figure 6A:
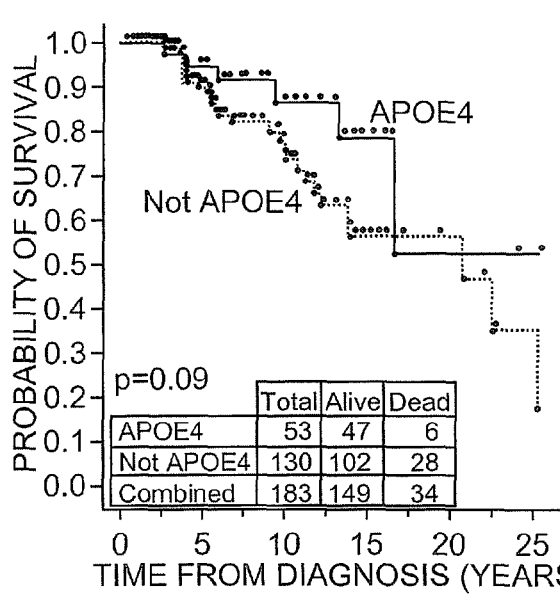
FIG. 6. APOE4, survival, and time-to-treatment (TTT). 6A. APOE4 and survival in all subjects (male and female). 6B. APOE4 and survival in all subjects (male and female). 6C. APOE4 and TTT in all subjects (male and female). 6D. APOE4 and TTT in all subjects (male and female).

A cohort of 183 CLL patients (50 females and 133 males) were followed in the Durham V.A. and Duke University Medical Centers (Table 1). Analysis of this cohort by gender revealed a profound survival benefit for female patients with an APOE4 genotype (i.e., possessing either one or two APOE4 alleles) (FIG. 1A), but there was no significant benefit for males (FIG. 1B). For the overall cohort (females and males together), APOE4 patients had longer survival than those with no APOE4 alleles (i.e., a non-APOE4 genotype) (FIG. 6A), but this difference for the population was not statistically significant. No statistically significant differences in survival were observed in any of these populations between APOE2 genotype and non-APOE2 genotype patients, or between APOE3 genotype and non-APOE3 genotype patients (data not shown). The long survival in APOE4 CLL patients is contrary to that of the general population, in which APOE4 genotype increases the risk for atherosclerosis and death from vascular disease (Davignon et al. (1999) Clin Chim Acta 286, 115-43).

Figure 1C:
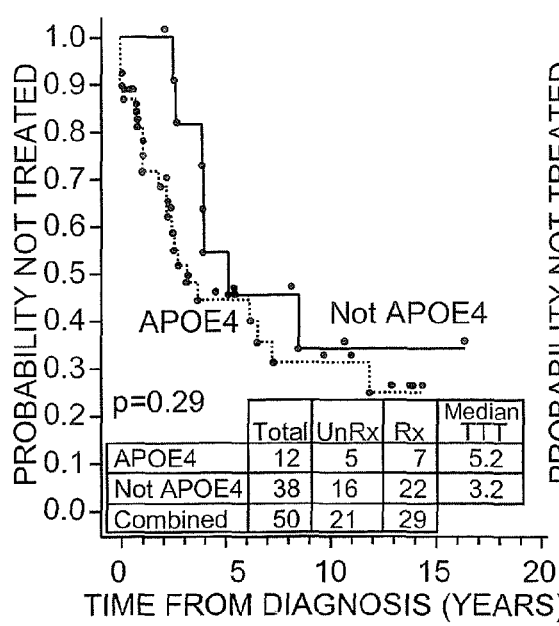
Figure 1D:
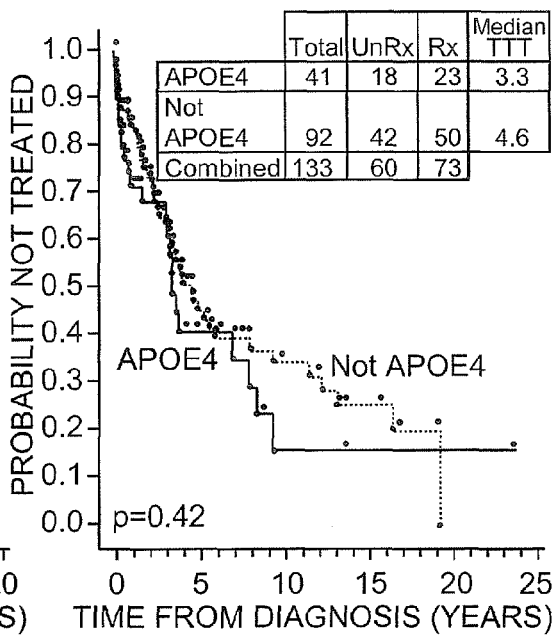
Figure 6B:
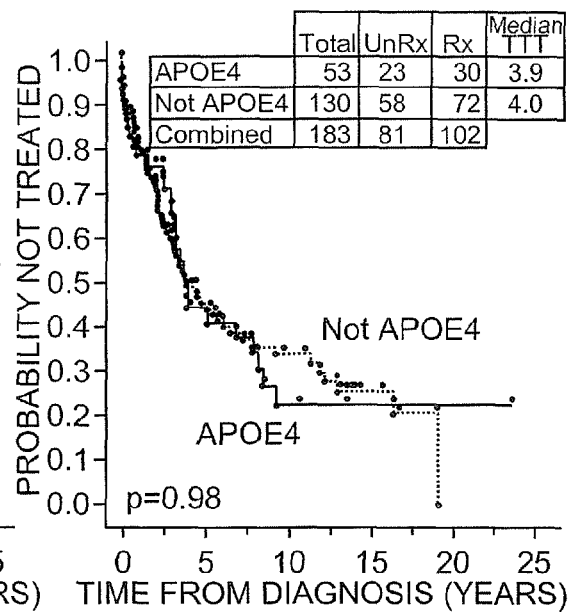

CLL is an incurable disease, and the decision to treat this leukemia is based on a variety of factors, including decline in other blood elements (development of anemia or thrombocytopenia), increasing lymphocyte count rates (e.g., a lymphocyte doubling time of less than 1 year), and systemic side effects such as fever and weight loss (Cheson et al. (1996) Blood 87, 4990-7). The time-to-treatment (TTT) from diagnosis therefore reflects the rate of disease progression. The presence or absence of an APOE4 allele did not alter TTT in females (FIG. 1C) or in males (FIG. 1D) separately or in the combined cohort of males and females (FIG. 6B). Of the APOE4 women, 7 of 12 received chemotherapy and none of 12 died. Of the non-APOE4 women, 22 of 38 received chemotherapy and 9 of 38 died.

Figure 2:
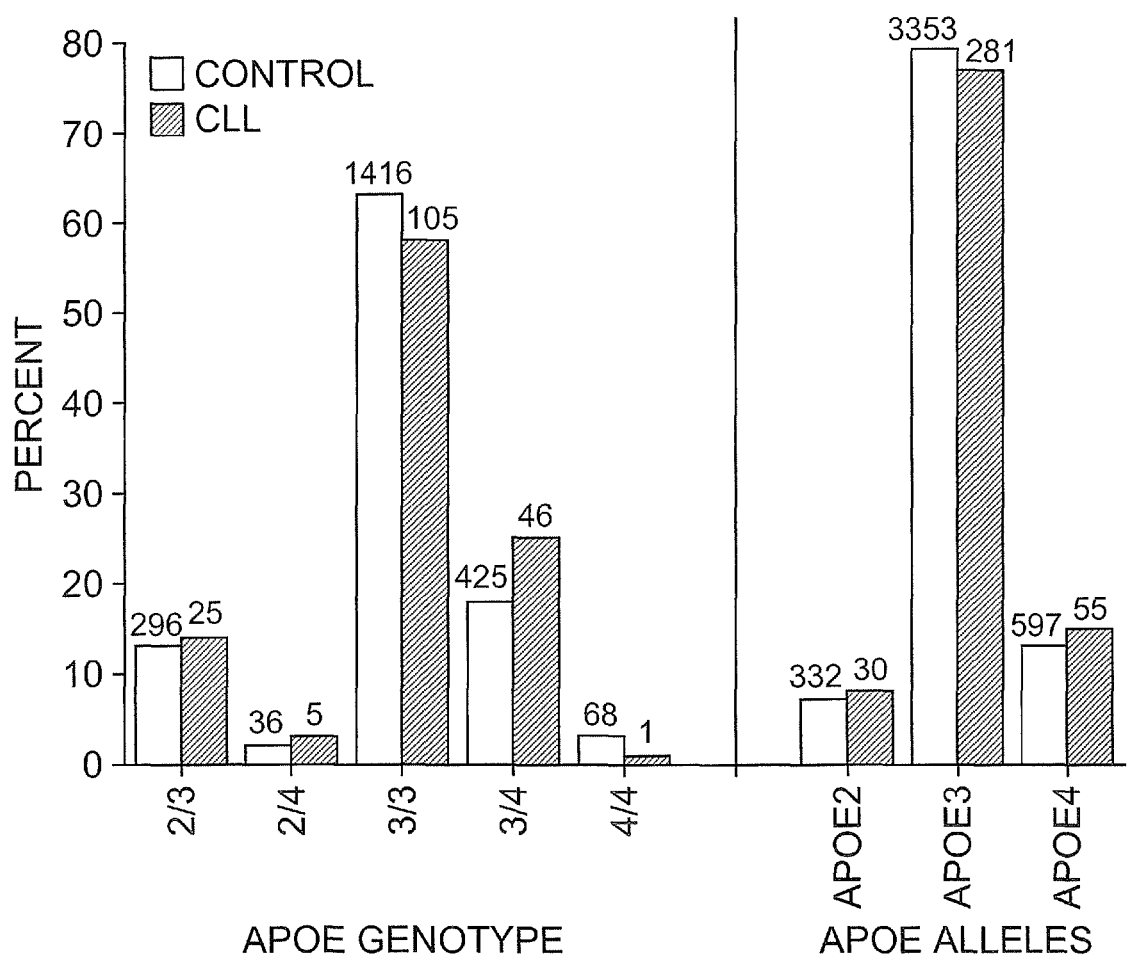
FIG. 2. Frequencies of APOE genotypes and alleles. Numbers above the bars represent numbers of subjects in that particular genotype. Control values are from reference number 27.
Figure 3A:
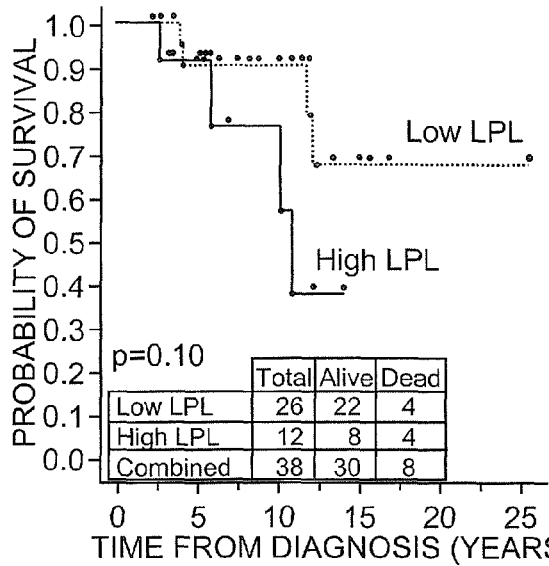
FIG. 3. Lipoprotein lipase (LPL), survival, and TTT. 3A. LPL and survival in women only. 3B. LPL and survival in men only. 3C. LPL and TTT in females. 3D. LPL and TTT in males.
Figure 3B:
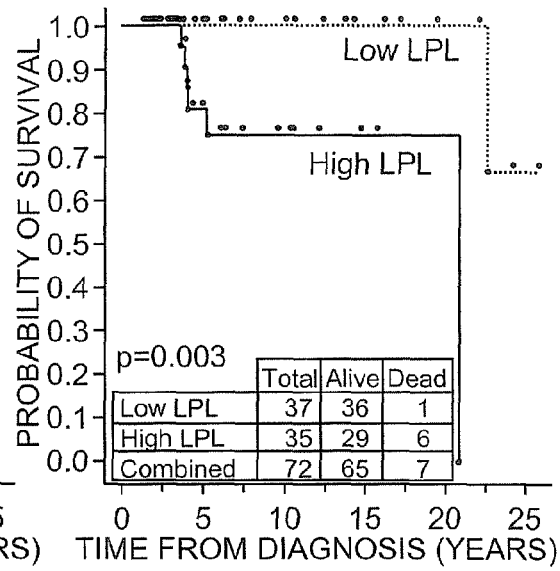
Figure 3C:
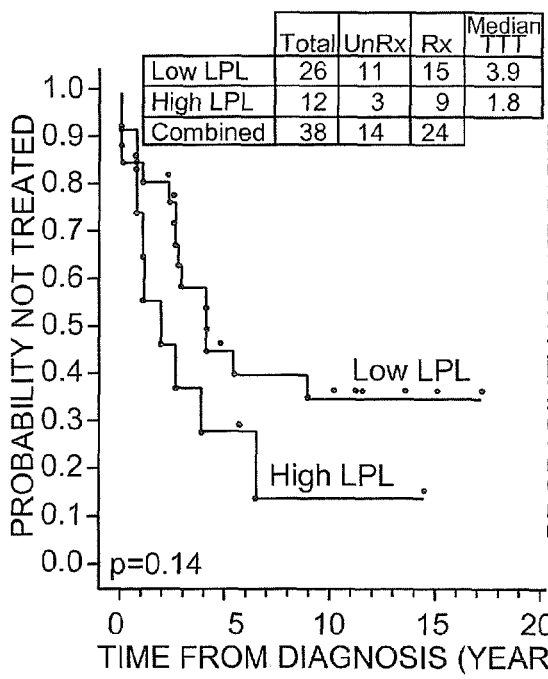
Figure 3D:
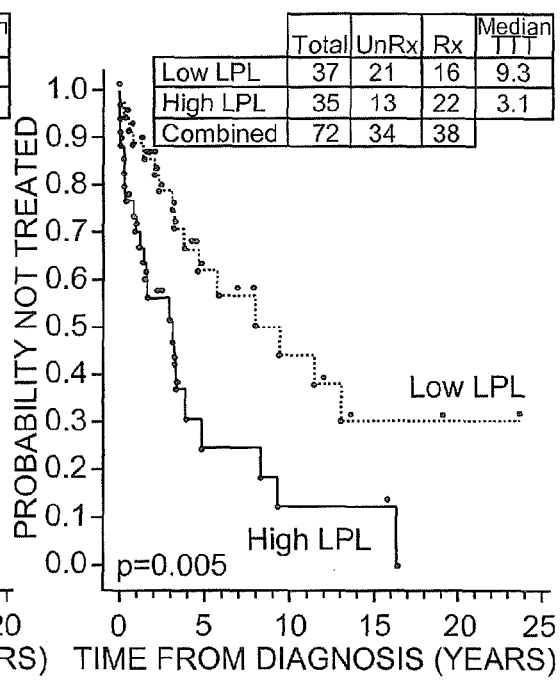

The APOE genotype distribution of the CLL patient population did not differ from that of the general population (Schaefer et al. (1994) Arterioscler Thromb 14, 1105-13) (FIG. 2). These data suggest that, although APOE genotype influences survival with CLL, it does not influence the risk of developing this disease.

Figure 6C:
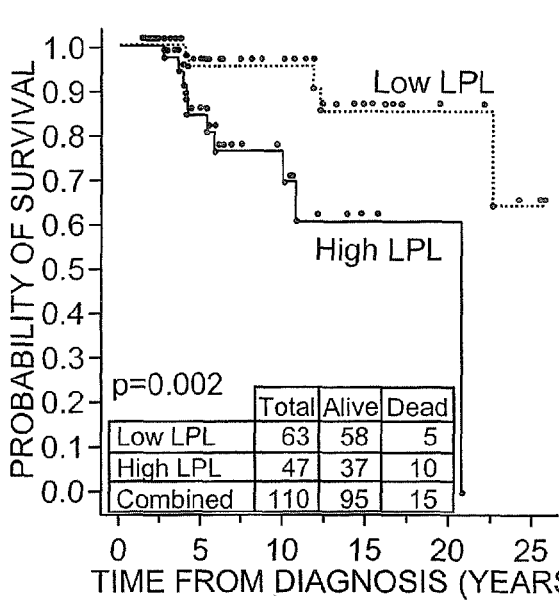
Figure 6D:
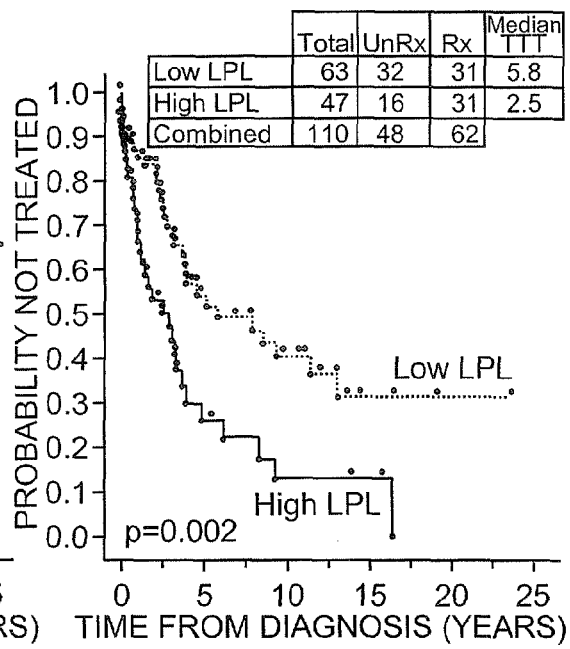

Lipoprotein lipase is a secreted enzyme that hydrolyzes phospholipids in VLDL particles, thereby increasing serum triglycerides and converting VLDL particles to LDL particles. In agreement with earlier publications (Oppezzo et al. (2005) Blood 106, 650-7; Nuckel et al. (2006) Leuk Lymphoma 47, 1053-61; Heintel et al. (2005) Leukemia 19, 1216-23), higher levels of leukemia cell LPL mRNA were significantly associated with a shorter survival and shorter TTT in the analysis of males and females in our CLL cohort independent of APOE status (FIG. 3A-D), but this was statistically significant only in males. Likewise, in analyzing the entire cohort of males and females together, those with high LPL mRNA levels had a significantly worse survival and TTT (FIGS. 6C and 6D).

We next analyzed survival of patients with CLL according to both APOE genotype and CLL cell LPL mRNA level (FIG. 4A-C). This co-analysis was possible in 110 of the 183 patients for whom enough mRNA was available for LPL analysis. APOE4 genotype patients with either low LPL or high LPL had much better survival (100%) than the non-APOE4 patients with either low LPL or high LPL. This was apparent when the population was considered as a whole (FIG. 4A), for females alone (FIG. 4B), or for males alone (FIG. 4C). These differences were statistically significant for the group as a whole and for men alone. These results suggest that APOE4 genotype has a stronger effect on survival than does LPL level.

TABLE 1

Patient characteristics-Duke University and V.A. Medical Centers

|  |  | Duke & V.A. |  | Duke only |  | V.A. only |
|---|---|---|---|---|---|---|
| Number | All | 183 | All | 125 | All | 58 |
| (percent) | M | 133 (73%)[a] | M | 77 (62%) | M | 56 (97%) |
|  | F | 50 (27%) | F | 48 (38%) | F | 2 (3%) |
| Age at diagnosis | All | 59 [52-66][b] | All | 59 [52-66] | All | 59 [52-64] |
| [$25^{th}$-$75^{th}$ percentile] | M | 60 [52-65] | M | 60 [51-66] | M | 59.5 [54-65] |
|  | F | 59 [52-68] | F | 59 [52-68] | F | 59 [43-75] |
| Rai stage at diagnosis | All | 116-34-21-4-8 | All | 83-22-14-4-2 | All | 33-12-7-0-6 |
| Stages 0-1-2-3-4 |  | (63%-19-11-2-4)[c] |  | (66%-18-11-3-2)[d] |  | (57%-21-13-0-10)[d] |
| Number | M | 80-27-17-1-8 | M | 52-18-11-1-2 | M | 33-12-7-0-6 |
| (Percent) |  | (60%-20-13-1-6)[e] |  | (62%-21-13-1-2) |  | (57%-21-12-0-10) |
|  | F | 36-7-4-3-4 | F | 36-8-4-3-1 | F | 1-1-0-0-0 |
|  |  | (72%-14-8-6-8)[e] |  | (69%-15-8-6-2) |  | (50%-50-0-0-0) |
| Length of follow-up | All | 6.1 [3.2-10.8] | All | 6.3 [3.4-10.8] | All | 5.5 [2.6-10.8] |
| Years [$25^{th}$-$75^{th}$ percentile] | M | 5.7 [3.0-10.2] | M | 6.2 [3.3-9.5] | M | 5.7 [2.7-10.8] |
|  | F | 7.2 [3.5-11.9] | F | 7.2 [3.4-12.0] | F | 6.4 [2.7-10.0] |
| Treated & Untreated | All | 102 & 81[a] | All | 69 & 56 | All | 33 & 25 |
|  |  | (56% & 44) |  | (55% & 44) |  | (57% & 43) |
|  | M | 73 & 60 | M | 45 & 39 | M | 33 & 25 |
|  |  | (55% & 45) |  | (54% & 46) |  | (57% & 43) |
|  | F | 29 & 21 | F | 30 & 22 | F | 1 & 1 |
|  |  | (58% & 42) |  | (58% & 42) |  | (50% & 50) |
| Died & Lived | All | 34 & 149[a] | All | 19 & 106 | All | 15 & 43 |
|  |  | (19% & 81) |  | (15% & 85) |  | (26% & 74) |
|  | M | 25 & 108 | M | 14 & 70 | M | 16 & 42 |
|  |  | (19% & 81) |  | (17% & 83) |  | (28% & 72) |
|  | F | 9 & 41 | F | 11 & 41 | F | 0 & 2 |
|  |  | (18% & 82) |  | (21% & 79) |  | (0% & 100%) |
| APOE allele frequency | All | 8, 77, 15 | All | 8, 76, 16 | All | 8, 79, 12 |
| (percent) |  | (366 alleles) |  | (250 alleles) |  | (116 alleles) |
| (E2, E3, E4) | M | 8, 76, 16 | M | 8, 73, 19 | M | 8, 80, 13 |
|  |  | (264 alleles) |  | (154 alleles) |  | (112 alleles) |
|  | F | 8, 80, 12 | F | 9, 80, 13 | F | 25, 75, 0 |
|  |  | (100 alleles) |  | (96 alleles) |  | (4 alleles) |
| LPL mRNA (units) | All | 3.36 [0.07-29.5][b] | All | 1.35 [0.07-21.7] | All | 8.88 [0.11-34.4] |
|  |  | (n = 85) |  | (n = 60) |  | (n = 25) |
|  | M | 4.81 [0.06-36.4] | M | 2.57 [0.15-18.48] | M | 10.95 [0.29-46.26] |
|  |  | (n = 69) |  | (n = 45) |  | (n = 24) |
|  | F | 0.98 [0.06-36.4] | F | 1.15 [0.07-37.25] | F | Not done |
|  |  | (n = 16) |  | (n = 15) |  |  |

[a]Number (percent)
[b]Median [$25^{th}$-$75^{th}$ percentile]
[c]Stages 0, 1, 2, 3, and 4 (percent at each stage)
[d]p = 0.04. Bold and underlined regions display the only values that are statistically significantly different (Chi square test)
[e]p = 0.02 (Chi square test)

Clinical stage, lymphocyte doubling time, immunoglobulin $IgV_H$ mutation status, cytogenetic abnormalities, and leukemia cell CD38 and Zap-70 expression are significantly associated with survival in CLL. Women with CLL and an APOE4 genotype compared to the non-APOE4 women patients had a significantly lower Rai stage, were less likely to have Zap-70 positive cells, had a higher hematocrit at the time of diagnosis, and had fewer deaths (Table 2). There were no differences in CD38 expression, $IgV_H$ mutational status, and cytogenetic abnormalities between women with and without the APOE4 genotype. High levels of LPL mRNA were significantly associated with unmutated $IgV_H$ status, CD38 positivity, Zap-70 positivity, advanced clinical stage, high serum LDH, and higher (worse) scores on a CLL prognostic index scale (Weinberg et al. (2007) Am J Hematol 82, 1063-1070) (Table 2).

TABLE 2

Patient characteristics - APOE4 and non-APOE4

| | | All | | APOE4 | | Non-APOE4 |
|---|---|---|---|---|---|---|
| Number | All | 183 (100%)[a] | All | 53 (100%) | All | 130 (100%) |
| | M | 133 (73%) | M | 41 (77%) | M | 92 (71%) |
| | F | 50 (27%) | F | 12 (23%) | F | 38 (29%) |
| Rai stage at diagnosis Stages 0-1-2-3-4 Number (Percent) | All | 116-34-21-4-8 (63%-19-11-2-4)[b] | All | 33-10-9-0-1 (62%-19-17-0-2) | All | 83-24-12-4-7 (64%-18-9-3-5) |
| | M | 80-27-17-1-8 (60%-20-13-1-6)[c] | M | 24-9-7-0-1 (59%-22-17-0-2) | M | 56-18-10-1-7 (61%-20-11-1-8) |
| | F | 36-7-4-3-4 (72%-14-8-6-8)[c] | F | 9-1-2-0-0 (75%-8-17-0-0) | F | 27-6-2-3-0 (71%-16-5-8-0) |
| Leukocyte DT (years) | All | 3.4 | All | 3.5 | All | 3.2 |
| | M | 3.5 [1.3-13.3][d] | M | 3.3 [1.4-12.7] | M | 3.6 [1.3-13.3] |
| | F | 2.9 [1.3-13.7] | F | 4.2 [1.4-13.7] | F | 2.1 [1.1-13.7] |
| $IgV_H$ Mutated & Unmutated | All | 112 & 63 (64% & 36) | All | 33 & 16 (67% & 33) | All | 79 & 47 (63% & 37) |
| | M | 82 & 44 (65 & 35) | M | 27 & 11 (71% & 29) | M | 55 & 33 (63% & 38) |
| | F | 30 & 19 (61% & 39) | F | 6 & 5 (55% & 45) | F | 24 & 14 (63% & 37) |
| CD38 positive & CD38 negative | All | 51 & 127 (29% & 71) | All | 11 & 40 (22% & 78) | All | 40-87 (32% & 69) |
| | M | 39 & 90 (30% & 70) | M | 10 & 29 (26% & 74) | M | 29 & 61 (32% & 68) |
| | F | 12 & 37 (24% & 76) | F | 1 & 11 (8% & 2%) | F | 11 & 26 (30% & 0) |
| Zap-70 positive & Zap-70 negative | All | 129 & 43 (75% & 25) | All | 33 & 14 (70% & 30) | All | 96 & 29 (77% & 23) |
| | M | 97 & 28 (78% & 22) | M | 28 & 7 (80% & 20) | M | 69 & 21 (77% & 23) |
| | F | 32 & 15 (68% & 32) | F | 5 & 7 (42% & 58)[e] | F | 27 & 8 (77% & 23)[e] |
| Cytogenetics Good & Bad | All | 77 & 14 (85% & 15) | All | 19 & 4 (83% & 17) | All | 58 & 10 (95% & 15) |
| | M | 56 & 8 (88% & 13) | M | 13 & 2 (87% & 13) | M | 43 & 6 (88% & 12) |
| | F | 21 & 6 (78% & 21) | F | 6 & 2 (75% & 25) | F | 15 & 4 (79% & 21) |
| Initial WBC ($\times 10^9$/L) | All | 22 [18.4-31] | All | 20 [16-27] | All | 24 [19-33] |
| | M | 22 [18.6-32.5] | M | 20 [15-29] | M | 24.5 [19-33.25] |
| | F | 21.5 [18.3-29.5] | F | 20 [18.75-23.5] | F | 23 [18.1-31.75] |
| Initial hematocrit (L/L × 100) | All | 42 [39-45] | All | 43 [39-45] | All | 42 [440-46] |
| | M | 43 [40-46] | M | 43 [41-47] | M | 43 [39-44] |
| | F | 41 [38-44] | F | 45 [43-46][f] | F | 39 [37-43][f] |
| Initial platelet count ($\times 10^9$/L) | All | 191 [152-243] | All | 183 [129-226] | All | 200 [163-249] |
| | M | 185 [147-232] | M | 183 [132-230] | M | 190 [160-244] |
| | F | 211 [173-255] | F | 190 [124-214] | F | 134 [185-256] |
| Treated & Untreated | All | 102 & 81 (56% & 44) | All | 30 & 23 (57% & 43) | All | 72 & 58 (55% & 45) |
| | M | 73 & 60 (55% & 45) | M | 23 & 18 (56% & 44) | M | 50 & 42 (54% & 46) |
| | F | 29 & 21 (58% & 42) | F | 7 & 5 (58% & 42) | F | 22 & 16 (58% & 42) |
| Died & Lived | All | 34 & 149 (19% & 81) | All | 6 & 47 (11% & 89) | All | 28 & 102 (22% & 78) |
| | M | 25 & 108 (19% & 81) | M | 6 & 35 (15% & 85) | M | 19 & 73 (21% & 79) |
| | F | 9 & 41 (18% & 82) | F | 0 & 12 (0% & 100)[g] | F | 9 & 29 (24% & 76)[g] |
| LPL mRNA (units) | All | 3.64 [0.07-30.00] n = 110 | All | 0.58 [0.05-11.70] n = 31[h] | All | 5.00 [0.15-43.33] n = 79[h] |
| | M | 5.00 [0.15-30.00] n = 73 | M | 1.33 [005-15.65] n = 21[i] | M | 9.40 [0.15-43.33] n = 51[i] |
| | F | 0.98 [0.06-36.38] n = 38 | F | 0.07 [0.04-2.14] n = 10[j] | F | 3.56 [0.11-47.85] n = 28[j] |

[a]Number (percent)
[b]Stages 0, 1, 2, 3, and 4 (percent at each stage)
[c]p = 0.02. Bold and underlined regions display the only values that are statistically significantly different (Chi square test)
[d]Median [$25^{th}$-$75^{th}$ percentile]
[e]p = 0.03 (Chi square test)
[f]p = 0.009 (Wilcoxon test)
[g]p = 0.02 (Chi square test)
[h]p = 0.054 (Wilcoxon test)
[i]p = 0.31 (Wilcoxon test)
[j]p = 0.057 (Wilcoxon test)

High LPL mRNA levels were also significantly associated with the cytogenetic abnormalities 17p13 del, trisomy 12, and 11q22 del, while low levels of LPL mRNA were significantly associated with the 13q14 del abnormality. APOE4 individuals tended to have lower LPL levels than non-APOE4 individuals, but the differences were not statistically significant (Table 3).

TABLE 3

Lipoprotein lipase correlations

|  |  | Number | LPL mRNA[1] | p value[2] |
|---|---|---|---|---|
| IgV$_H$ mutation status vs LPL mRNA | Mutated | 67 | 0.46 (0.02-7.3) | <0.0001 |
|  | Unmutated | 42 | 18.1 (3.1-56.5) |  |
| CD38 vs LPL mRNA | Positive | 23 | 30.9 (0.8-65.6) | 0.002 |
|  | Negative | 86 | 1.2 (0.1-14.2) |  |
| Zap-70[3] vs LPL mRNA | Positive | 69 | 12.6 (0.4-48.1) | 0.0006 |
|  | Negative | 38 | 0.4 (0.1-6.5) |  |
| Serum LDH vs LPL mRNA | High | 27 | 13.6 (1.0-61.6) | 0.009 |
|  | Normal | 75 | 1.2 (0.1-16.0) |  |

TABLE 3-continued

Lipoprotein lipase correlations

|  |  | Number | LPL mRNA[1] | p value[2] |
|---|---|---|---|---|
| Cytogenetics vs LPL mRNA | Good[4] | 43 | 0.3 (0.02-9.4) | 0.004 |
|  | Bad | 8 | 15.1 (11.9-60.2) |  |
|  | 13q14 del | 24 | 0.1 (0.04-1.2) | 0.04 |
|  | Not 13q14 del | 27 | 9.4 (0.1-30.9) |  |
|  | 17p13 del | 4 | 54.6 (19.6-101.0) | 0.02 |
|  | Not 17p13 del | 47 | 0.4 (0.04-12.5) |  |
|  | Trisomy 12 | 6 | 29.2 (7.1-109.3) | 0.02 |
|  | Not Trisomy 12 | 45 | 0.4 (0.03-12.5) |  |
| CLL prognosis score[5] | 0 | 44 | 0.5 (0.03-7.7) | 0.003 |
|  | 1 | 29 | 2.6 (0.3-22.5) |  |
|  | 2 | 22 | 41.7 (0.5-71.3) |  |
|  | 3 | 5 | 50.5 (6.8-59.6) |  |

[1]Units (see methods section)
[2]Wilcoxon test
[3]Zap-70 determined by immunoblot (8)
[4]Cytogenetic abnormalities determined by FISH analysis. "Good" included 13q14 del and normal. "Bad" included 17p13 del, 11q22 del, trisomy 12, and complex abnormalities.
[5]CLL prognosis score derived from clinical stage, CD38 expression, and serum LDH (8).

TABLE 4

Additional Patient Characteristics - Race, Drug Rx, Hormonal Rx

Race

|  | African American |  | Caucasian |  | Hispanic |  | Indian |  | Unknown |  | Total |
|---|---|---|---|---|---|---|---|---|---|---|---|
| All | 19 | 10.4% | 160 | 87.9% | 1 | 0.5% | 1 | 0.5% | 1 | 0.5% | 182 |
| Men | 11 | 8.3% | 118 | 89.4% | 1 | 0.8% | 1 | 0.8% | 1 | 0.8% | 132 |
| Women | 8 | 16.0% | 42 | 84.0% | 0 | 0.0% | 0 | 0.0% | 0 | 0.0% | 50 |
| E4 | 4 | 7.7% | 47 | 90.4% | 0 | 0.0% | 1 | 1.9% | 0 | 0.0% | 52 |
| non E4 | 15 | 11.5% | 113 | 86.9% | 1 | 0.8% | 0 | 0.0% | 1 | 0.8% | 130 |
| E4 Women | 1 | 8.3% | 11 | 91.7% | 0 | 0.0% | 0 | 0.0% | 0 | 0.0% | 12 |
| non E4 women | 7 | 18.4% | 31 | 81.6% | 0 | 0.0% | 0 | 0.0% | 0 | 0.0% | 38 |
| E4 men | 3 | 7.5% | 36 | 90.0% | 0 | 0.0% | 1 | 2.5% | 0 | 0.0% | 40 |
| non E4 men | 8 | 8.7% | 82 | 89.1% | 1 | 1.1% | 0 | 0.0% | 1 | 1.1% | 92 |

Drug Rx

|  | E4 | non E4 | E4 women | non E4 women |
|---|---|---|---|---|
| Fludarabine | 11 | 44 | 2 | 12 |
|  | 21.2% | 33.8% | 16.7% | 31.6% |
| Cyclophosphamide | 6 | 23 | 2 | 5 |
|  | 11.5% | 17.7% | 16.7% | 13.2% |
| Rituximab | 10 | 33 | 2 | 10 |
|  | 19.2% | 25.4% | 16.7% | 26.3% |
| Alemtuzumab | 2 | 6 | 0 | 2 |
|  | 3.8% | 4.6% | 0.0% | 5.3% |
| Chlorambucil | 20 | 48 | 5 | 17 |
|  | 38.5% | 36.9% | 41.7% | 44.7% |
| No Rx | 30 | 72 | 5 | 16 |
|  | 57.7% | 55.4% | 41.7% | 42.1% |
| Total | 52 | 130 | 12 | 38 |

Hormonal Rx

|  | E4 women | non E4 women |
|---|---|---|
| Climara | 0 | 1 |
|  | 0.0% | 0.8% |
| Est patch/Provera | 0 | 3 |
|  | 0.0% | 2.3% |
| Est vaginal | 1 | 0 |
|  | 1.9% | 0.0% |
| Est/Provera | 1 | 0 |
|  | 1.9% | 0.0% |
| Estrogen | 0 | 2 |
|  | 0.0% | 1.5% |
| Estrogen patch | 0 | 1 |
|  | 0.0% | 0.8% |

TABLE 4-continued

Additional Patient Characteristics - Race, Drug Rx, Hormonal Rx

| | | |
|---|---|---|
| Estrogen vaginal | 0 | 3 |
| | 0.0% | 2.3% |
| Premarin | 1 | 5 |
| | 1.9% | 3.8% |
| Premarin/Provera | 2 | 3 |
| | 3.8% | 2.3% |
| Any Hormonal Rx | 5 | 18 |
| | 9.6% | 13.8% |
| Total | 52 | 130 |

Discussion.

We observe here that the APOE4 genotype is associated with markedly increased survival in female CLL patients, but not with the length of time before treatment is required (TTT). These observations suggest that the APOE4 genotype enhances responses to therapy. Therapies commonly employed in CLL trigger apoptosis of these cells (Keating, M. J. (2002) in Leukemia, eds. Henderson et al. (Saunders, Philadelphia), pp. 131-151; Schwarz et al. (2001) in The chemotherapy source book, ed. Perry, M. C. (Lippincott Williams & Wilkins, Philadelphia), pp. 1-6). Since apoE4-VLDL increases the apoptosis of endothelial cells initiated by withdrawing growth factors (DeKroon et al. (2006) Circ Res 99, 829-36), it may similarly increase apoptosis of CLL cells exposed to therapeutic drugs.

Without wishing to be bound to any particular theory, it is thought that the APOE4 allele specificity reported here results from apoE isoform-selective binding of VLDL to cell surface receptors. In endothelial cells, apoE4-VLDL is pro-apoptotic through its interaction with an as yet unidentified cell surface receptor that is inhibited by the receptor-associated protein (RAP). RAP inhibits binding of apoE both to LDL-family receptor members and to heparan sulfate proteoglycans on the cell surface (DeKroon et al. (2003) J Lipid Res 44, 1566-73; Ji et al. (1998) J Biol Chem 273, 13452-60). ApoE4-VLDL binding to CLL cells may enhance leukemia cell apoptosis initiated by various means (e.g., chemotherapy) and improve overall survival.

Figure 5:
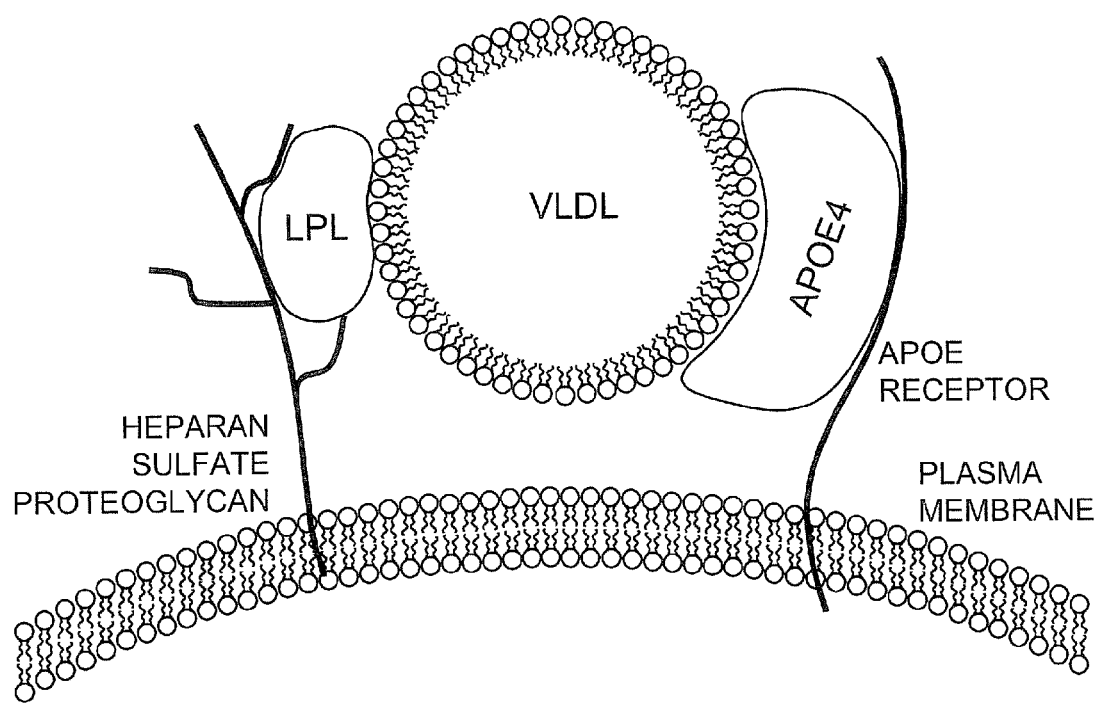
FIG. 5. Proposed model of CLL and the interaction of ApoE4-VLDL and LPL via cell surface receptors. ApoE4-VLDL tethers to a cell surface receptor (either a heparan sulfate proteoglycan or an LDL-receptor family member) thereby recruiting SHIP-2, which in turn increases cell apoptosis (4). VLDL particles are converted to LDL particles by the lipase activity of LPL that can also bind to cell surface heparan sulfate proteoglycans. CLL patients with an APOE4 genotype (but not APOE2 or APOE3 genotype) would thus have increased apoptosis of their leukemia cells induced by ApoE4-VLDL and better prognosis, while patients with high LPL levels would have lower ApoE4-VLDL, less apoptosis of leukemia cells, and worse prognosis.

Elevated LPL mRNA or LPL protein levels are associated with poorer prognosis in CLL (Oppezzo et al. (2005) Blood 106, 650-7; Nuckel et al. (2006) Leuk Lymphoma 47, 1053-61; Heintel et al. (2005) Leukemia 19, 1216-23). LPL is a secreted lipase that binds heparan sulfate proteoglycans on the cell surface. Furthermore, LPL binds to VLDL particles (that also bind cell surface heparan sulfate proteoglycans) and hydrolyzes VLDL triglycerides (FIG. 5) (Mulder, M., Lombardi, P., Jansen, H., van Berkel, T. J., Frants, R. R. & Havekes, L. M. (1993) J Biol Chem 268, 9369-75). LPL thereby converts VLDL particles to LDL particles and increases serum fatty acids. Elevated LPL enzymatic activity would therefore increase the rate of conversion of VLDL to LDL. The deleterious effects of elevated LPL activity on survival in CLL may be due to the reduced abundance of apoE4-VLDL particles, a condition that would lead to decreased apoptosis.

Figure 7A:
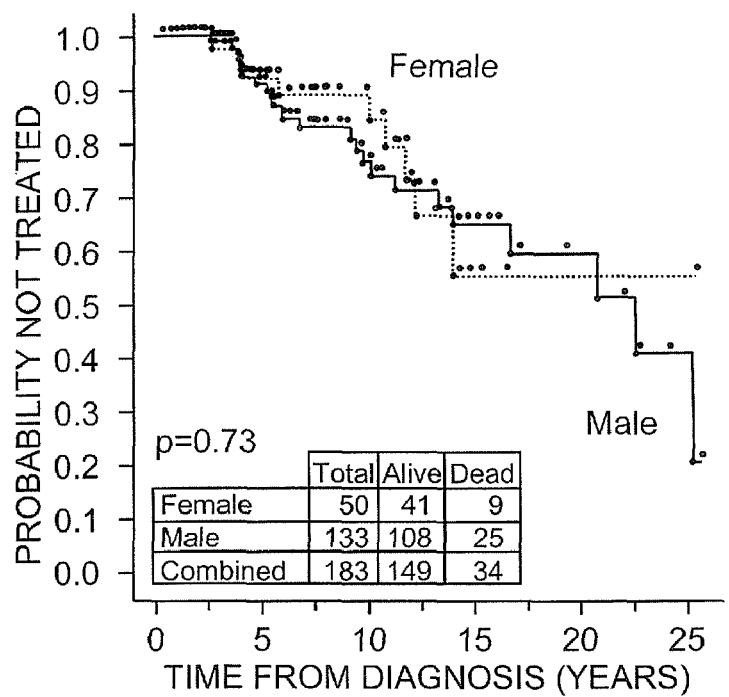
FIG. 7. Survival and TTT in women and men with CLL. 7A. Survival in the entire cohort of patients with and without an APOE4 allele. 7B. TTT in the entire cohort of patients with and without an APOE4 allele.
Figure 7B:
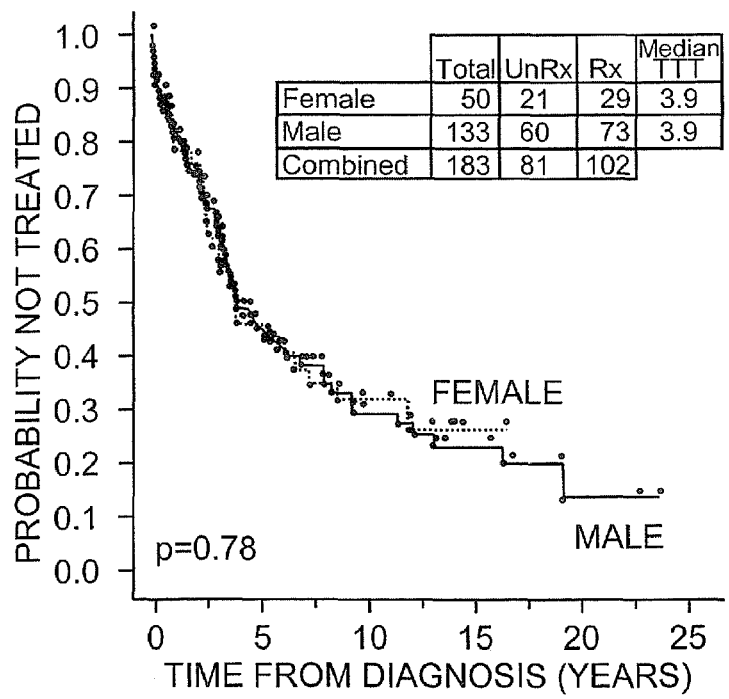

Several groups have reported that women have a slightly longer survival than men in CLL (see Molica, S. (2006) Leuk Lymphoma 47, 1477-1480 for review), but this was not the case in our cohort (FIG. 7). We did note, however, that the effect of the APOE4 allele on survival is much more pronounced in women, while the effect of LPL levels on survival is more pronounced in men. Women with CLL generally present with fewer unfavorable clinical features, and respond better to treatment (Molica, S. (2006) Leuk Lymphoma 47, 1477-1480).

The female-specific protective effective of the APOE4 genotype on survival in CLL could relate to several mechanisms, including modulation of CLL cell apoptosis by estrogen through the apoE/Akt pathway. In our cohort, 92% of the women with CLL and an APOE4 genotype were postmenopausal at the time of diagnosis, but most were taking hormonal replacement therapy. Of the 50 women (range of age at diagnosis 42-85 yr), 45 were post-menopausal, and 23 of 25 (on whom information was available) were receiving hormonal replacement therapy. Estrogens can be cytotoxic for CLL cells in vitro (Huang et al. (2000) Nature 407, 390-5), and diethylstilbestrol treatment of prostate cancer in patients with CLL has been reported to reduce blood CLL cell counts (Narasimhan et al. (1980) Am J Hematol 8, 369-75). Several physiological metabolites of endogenous estrogen (including 2-methoxy-estradiol) induce apoptosis of leukemia cells by inactivating Akt (Gao et al. (2005) Oncogene 24, 3797-809). Estrogen receptor agonists stimulate PIP3 synthesis and enhances Akt phosphorylation in endothelial cells (Haynes et al. (2000) Circ Res 87, 677-82). We have shown that Akt phosphorylation is inhibited by APOE4-VLDL (DeKroon et al. (2006) Circ Res 99, 829-36). Estrogen regulates APOE expression (Wang et al. (2006) Proc Natl Acad Sci USA 103, 16983-8). Androgen interacts with apolipoprotein genotype, protecting against APOE4-induced cognitive deficits (Raber et al. (2002) J Neurosci 22, 5204-9). The APOE genotype alters lipoprotein particle distribution and number, and triglyceride metabolism, and gender differences in these effects have been reported (Dallongeville et al. (1992) J Lipid Res 33, 447-5426; Ferrieres et al. (1994) Arterioscler Thromb 14, 1553-60). These observations point to a female-specific protective effective of the APOE4 genotype on survival in CLL that relates to the modulation of CLL cell apoptosis by estrogen through the apoE/Akt pathway.

APOE genotyping of patients with CLL provides important clinical prognostic information. The allele-specific influence of APOE on disease progression also provides important new insights into the mechanisms of disease and response to therapy.

The frequency of the APOE alleles in the CLL patient population was identical to that of control populations. APOE genotype therefore does not appear to affect susceptibility to CLL, but influences the clinical course of disease, particularly after therapy is initiated. In contrast, APOE genotype does influence susceptibility to other diseases, most notably Alzheimer's, in which APOE4 markedly increases risk (Saunders et al. (1993) Neurology 43, 1467-72).

Materials and Methods.

Patients with CLL were recruited from the Duke University and V.A. Medical Centers from July 1999 through August 2006 as previously described (Weinberg et al. (2007) Am J Hematol 82, 1063-1070). The 183 patients studied here [from the cohort of 190 patients we reported earlier (Weinberg et al. (2007) Am J Hematol 82, 1063-1070)] were those from whom we had sufficient DNA to genotype for APOE. Fifty-eight patients (32%) were from the Durham V.A. Medical Center, and 125 patients (68%) were from Duke University Medical Center. One hundred thirty-three patients (73%) were male. Diagnosis and staging of CLL, and decisions regarding initiation of treatment were determined according to NCI Working Group criteria (Cheson et al. (1996) Blood 87, 4990-7; Weinberg et al. (2007) Am J Hematol 82, 1063-1070). The length of time from diagnosis to death from any cause was defined as overall survival, and the length of time to initiation of treatment from the date of diagnosis was defined as the time-to-treatment. All subjects had not received CLL therapy for at least 4 weeks before blood was sampled, and all patients gave informed consent according to protocols approved by the V.A. and Duke University Institutional Review Boards.

Blood anticoagulated with sodium heparin was processed to enrich the CLL cells by negative selection using monoclonal antibodies as previously described (Volkheimer et al. (2007) Blood 109, 1559-67; Weinberg et al. (2007) Am J Hematol 82, 1063-1070). The enriched CLL cells contained 0.9±0.1% (mean±SEM) T cells and 3.4±0.6% $CD19^+/CD5^-$ cells ("normal" B cells). Purified cells were immunophenotyped on the day of isolation, and some were frozen for later analyses. Doubling times, CLL cell phenotypes including CD38 and Zap-70 assessment, $IgV_H$ mutation status, and FISH analyses were performed as we have previously described (Volkheimer et al. (2007) Blood 109, 1559-67; Weinberg et al. (2007) Am J Hematol 82, 1063-1070).

APOE genotyping was performed as previously described (Saunders et al. (1993) Neurology 43, 1467-72). We assayed LPL mRNA by quantitative RT-PCR using TaqMan pre-made primers (Applied Biosystems) for lipoprotein lipase (LPL) and β-actin (ACAB) genes. cDNA was synthesized with the high capacity archive kit (Applied Biosystems) using a minimum of 50 ng of RNA. cDNA was amplified using the TaqMan Universal 2×PCR mix (Applied Biosystems). Standard semi-logarithmic curves for each LPL and ACAB determination, correlating RNA concentration and Ct values, were constructed for each experiment using a standard preparation of highly purified RNA obtained from pheresisisolated lymphocytes (Mihovilovic et al. (1993) Methods Neurosc 12, 169-190). LPL values were normalized using its corresponding ACAB value. All samples were determined in duplicate. We dichotomized LPL values with receiver-operator-characteristics (ROC) curve analysis using "good" and "poor" prognosis groups. "Good" prognosis was defined as not requiring treatment for >5.5 years from diagnosis (the $75^{th}$ percentile for time-to-treatment), and "bad" prognosis was defined as requiring treatment within <2.6 years from diagnosis (the $50^{th}$ percentile for time-to-treatment). The ROC-determined LPL cutoff value was 6.2 units, with an area under the curve of 0.73. Comparisons of clinical and laboratory parameters between groups were done using the Wilcoxon's test and the chi square test as appropriate. Survival and time-to-treatment Kaplan-Meier data were analyzed using the log rank test. A two-sided alpha of 0.05 was used for all tests.

EXAMPLE 2

We determined if estrogen receptor agonists [2-methoxyestradiol (2-ME) and diethylstilbesterol (DES)] and mixed agonist-antagonist [tamoxifen (TAM)] could kill CLL cells in vitro. Freshly isolated CLL cells were incubated 72 hours with 2-ME, DES, and TAM at various concentrations. Then the cytotoxicity of the agents was determined.

All were cytotoxic for the CLL cells. The effective dose for 50% killing (ED50) for each was 7.5 µM (2-ME), 8.2 µM (DES), and 6.5 µM (TAM). At 10 µM, the percent cytotoxicity for each was 71% (2-ME), 79% (DES), and 99% (TAM).

EXAMPLE 3

Figure 8:
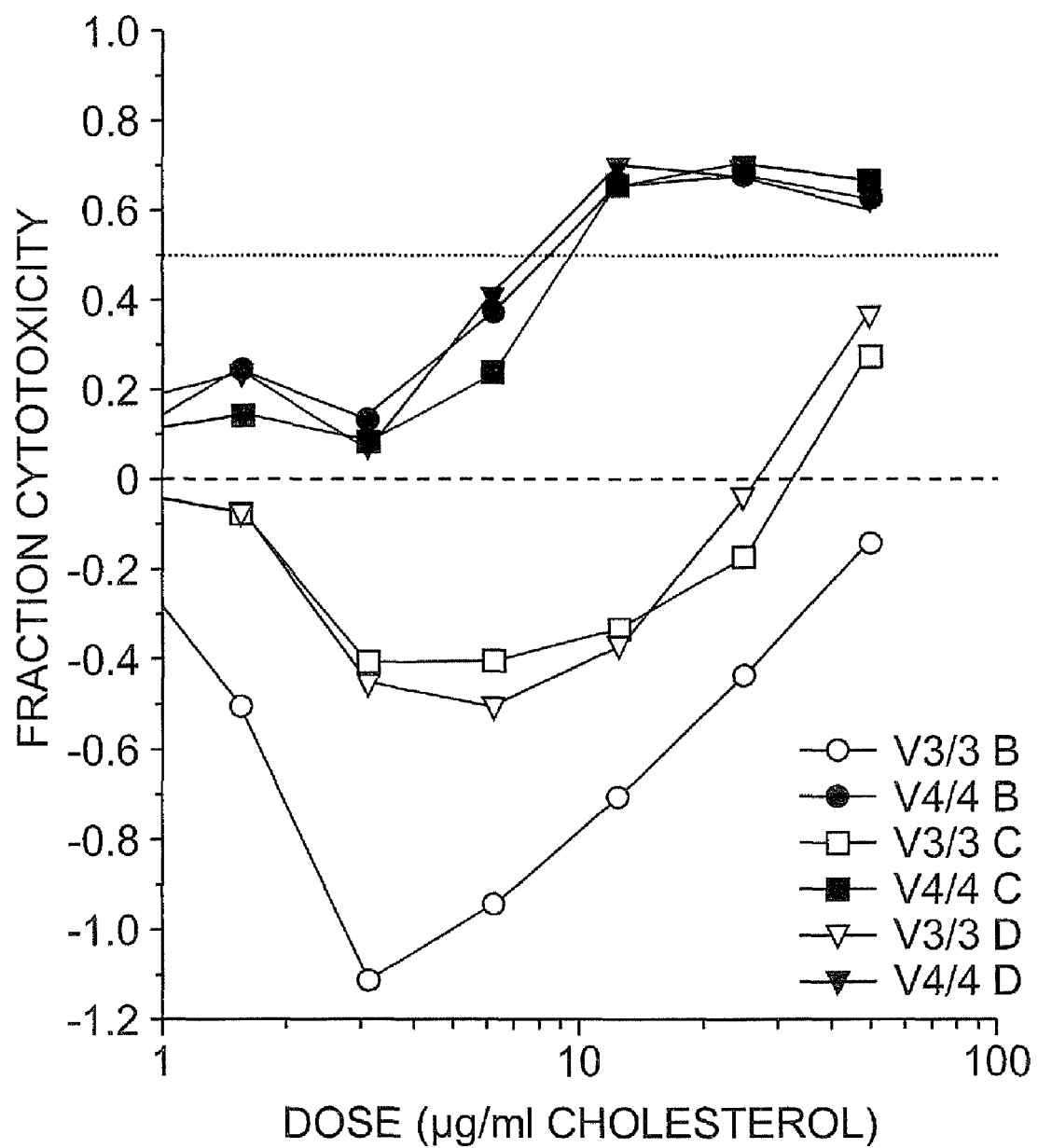
FIG. 8. Cytotoxicity for CLL cells from 3 patients (patients "B," "C," and "D") of VLDL purified from an individual of APOE3 homozygous genotype ("V3/3") and an individual of APOE4 homozygous genotype ("V4/4"). The lower dotted line denotes zero cytotoxicity, and the upper dotted line denotes 0.5 fraction of cytotoxicity. A fraction of cytotoxicity of 1.0 signifies 100% cytotoxicity, and a fraction of cytotoxicity of 0.5 signifies 50% cytotoxicity. VLDL-apoE4/4 was very cytotoxic for CLL cells (fraction cytotoxicity maximum of 0.65 to 0.75, but VLDL-apoE3/3 displayed minimal cytotoxicity even at the highest concentrations. At low concentrations, VLDL-apoE3/3 was cytoprotective for the CLL cells. This signifies that it enhanced viability of the CLL cells.

Experiments were performed to determine if apoE4 and apoE3 isolated from plasma of humans who were homozygous for APOE4 or APOE3 were cytotoxic for freshly purified CLL cells from patients with CLL (FIG. 8). VLDL was purified by centrifugation of plasma (over potassium bromide gradients) from individuals who were either homozygous APOE4 ("4/4") or APOE3 ("3/3"). VLDL was measured as µg/ml cholesterol. Cells were purified using "Rosette-Sep" for B cells (Stem Cell Technologies, Vancouver, British Columbia), and were >97% pure CLL cells. Cytotoxicity was determined using the MTS calorimetric assay (Promega, Madison, Wis.) after 72 hours' culture in vitro.

Results showed that very low density lipoprotein (VLDL)-apoE4 was directly cytotoxic for CLL cells in vitro. VLDL is the major source of plasma apoE4. However, VLDL-apoE3 was only minimally cytotoxic for CLL cells, and at low concentrations of VLDL-apoE3, it was protective for CLL cells (it enhanced cell viability). In parallel experiments, it was demonstrated that CLL cells incubated with VLDL-apoE4 had diminished levels of phosphorylated Akt, compared to control cells or those treated with VLDL-apoE3. While not wishing to be bound by theory, it is generally thought that phosphorylated Akt is anti-apoptotic and life-promoting for CLL cells, and that dephosphorylated Akt enhances apoptosis and death of CLL cells.

These results indicate that VLDL-apoE4 or mimetics of VLDL-apoE4 may be useful as a cytotoxic treatment for CLL. VLDL-apoE4 (or a mimetic) could be administered as a purified agent orally or parenterally. Also, agents that would increase concentrations of VLDL-apoE4 should be cytotoxic for CLL cells. Alternatively, antagonists of VLDL-apoE3 or agents that reduce concentrations of VLDL-apoE3 should reduce the viability and numbers of CLL cells.

The foregoing is illustrative of the present invention, and is not to be construed as limiting thereof. The invention is defined by the following claims, with equivalents of the claims to be included therein.

That which is claimed is:

1. A method of treating a subject afflicted with chronic lymphocytic leukemia comprising administering to said subject VLDL-apoE4 in an amount effective to treat said chronic lymphocytic leukemia.

2. The method of claim 1, further comprising the step of detecting the presence or absence of an APOE4 allele in a biological sample of said subject.

3. The method of claim 2, wherein said detecting step is carried out by genotyping.

4. The method of claim 1, wherein said administering step is carried out by oral administration.

5. The method of claim 1, wherein said administering step is carried out by parenteral administration.

6. A method of treating a subject afflicted with chronic lymphocytic leukemia comprising administering to said subject VLDL-apoE4 in combination with administering to said subject an estrogenic agent or androgen withdrawal agent, the two combined in an amount effective to treat said chronic lymphocytic leukemia.

7. The method of claim 6, further comprising the step of detecting the presence or absence of an APOE4 allele in a biological sample of said subject.

8. The method of claim 7, wherein said detecting step is carried out by genotyping.

9. The method of claim 6, wherein said administering step is carried out by oral administration.

10. The method of claim 6, wherein said administering step is carried out by parenteral administration.

11. The method of claim 6, wherein said subject is a human subject.

12. The method of claim 6, wherein said administering is carried out simultaneously or sequentially.

13. The method of claim 1, wherein said subject is a human subject.

14. The method of claim 1, wherein said subject is a female subject.

15. The method of claim 1, wherein said subject is a male subject.

* * * * *